(12) United States Patent  (10) Patent No.: US 6,368,342 B1
Lemer  (45) Date of Patent: Apr. 9, 2002

(54) STRERNUM CLOSURE DEVICE AND PINCERS FOR MOUNTING STAPLES AND APPROXIMATOR BRACKETS

(75) Inventor: Joseph Lemer, Haifa (IL)

(73) Assignee: Haifa Surgical Instruments Ltd., Haifa (IL)

( * ) Notice: Subject to any disclaimer, the term of this patent is extended or adjusted under 35 U.S.C. 154(b) by 0 days.

(21) Appl. No.: 09/905,064

(22) Filed: Jul. 13, 2001

Related U.S. Application Data

(63) Continuation-in-part of application No. 09/799,475, filed on Mar. 5, 2001, which is a continuation-in-part of application No. 09/626,802, filed on Jul. 27, 2000.

(51) Int. Cl.[7] .......................... A61B 17/04; F16B 15/00
(52) U.S. Cl. ...................... 606/216; 227/19; 227/175.1; 411/457
(58) Field of Search ................................ 606/216, 220; 227/19, 175.1; 411/457

(56) References Cited

U.S. PATENT DOCUMENTS

| 408,080 A | * | 7/1889 | Carroll ........................ 606/218 |
| 4,122,989 A | | 10/1978 | Kapitanov et al. .......... 227/108 |
| 4,201,215 A | * | 5/1980 | Crossett et al. ............. 606/215 |
| 4,481,960 A | | 11/1984 | Brooks ........................ 131/336 |
| 4,512,346 A | | 4/1985 | Lemole ....................... 128/335 |
| 4,585,341 A | | 4/1986 | Woodfield ................. 356/28.5 |
| 5,163,698 A | * | 11/1992 | Peters et al. ................. 227/176 |
| 5,263,973 A | * | 11/1993 | Cook .......................... 606/219 |
| 5,342,396 A | | 8/1994 | Cook .......................... 606/219 |
| 5,356,417 A | | 10/1994 | Golds ......................... 606/151 |
| 5,462,542 A | | 10/1995 | Alesi, Jr. .................... 606/151 |
| 5,667,527 A | | 9/1997 | Cook .......................... 606/219 |
| 5,849,012 A | | 12/1998 | Abboudi ...................... 606/54 |
| 6,007,538 A | | 12/1999 | Levin .......................... 606/71 |
| 6,030,410 A | | 2/2000 | Zurbrugg .................... 606/219 |

* cited by examiner

Primary Examiner—Gary Jackson
(74) Attorney, Agent, or Firm—Rashida A. Karmali

(57) ABSTRACT

A sternum closure device for securing parts of severed sternum, such as a human sternum following surgery. The device includes an anvil, capable of forming staples, a bracket positioned, opposite the anvil, an instrument for creating openings in the sternum a clamping mechanism and a mechanism for feeding, mounting and applying the staples. The bracket is joined with the anvil through a displacement mechanism. The instrument for forming opening is designed as a bit brace having a reducing gear and two chucks, to enable concurrent drilling of openings in both severed parts of the severed sternum. The mechanism for feeding and mounting the staples comprises a ribbed bed, a cartridge containing staples and an instrument for mounting the staples. The clamping means enables drilling of openings in both severed parts of sternum, and feeding and mounting the staples. Specially designed pincers are also provided for mounting the staples and other special staples. A plurality of approximator brackets are provided for holding two halves of a severed sternum for stapling.

25 Claims, 19 Drawing Sheets

View A

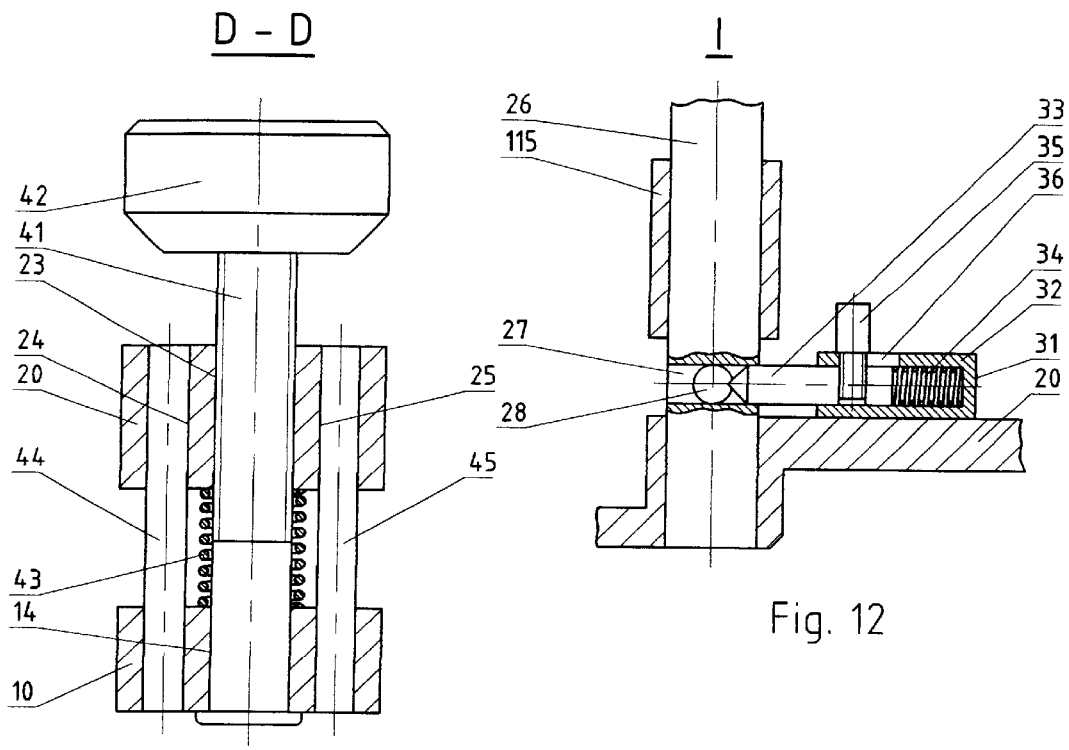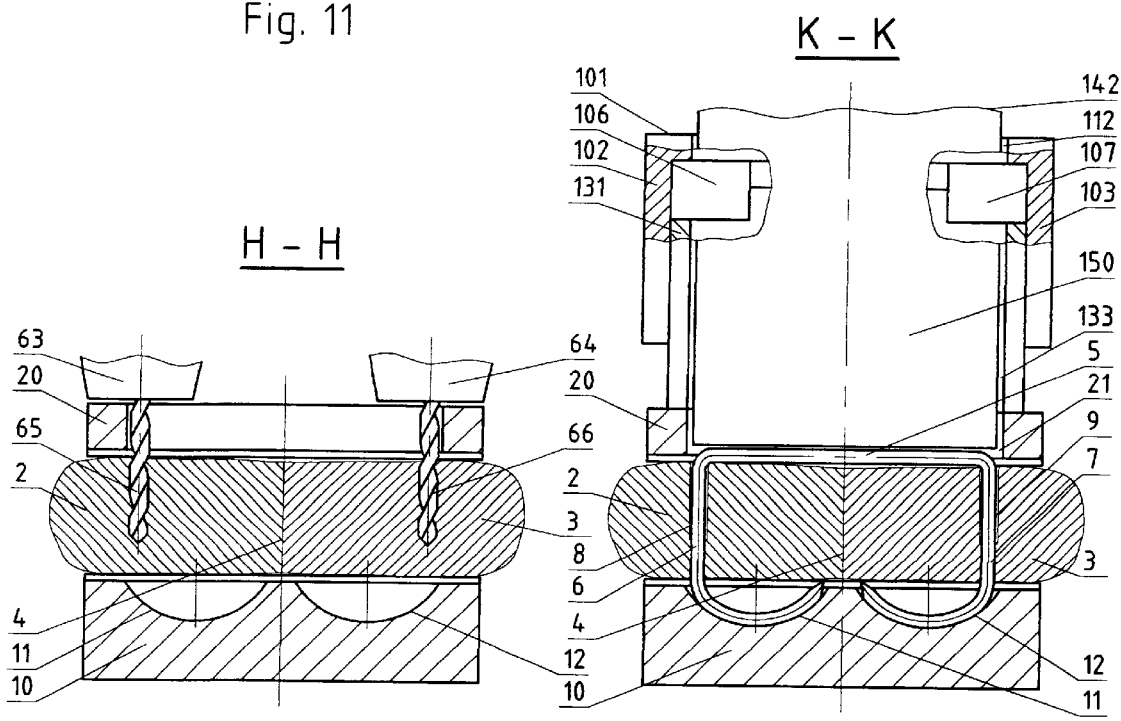

View L

View M

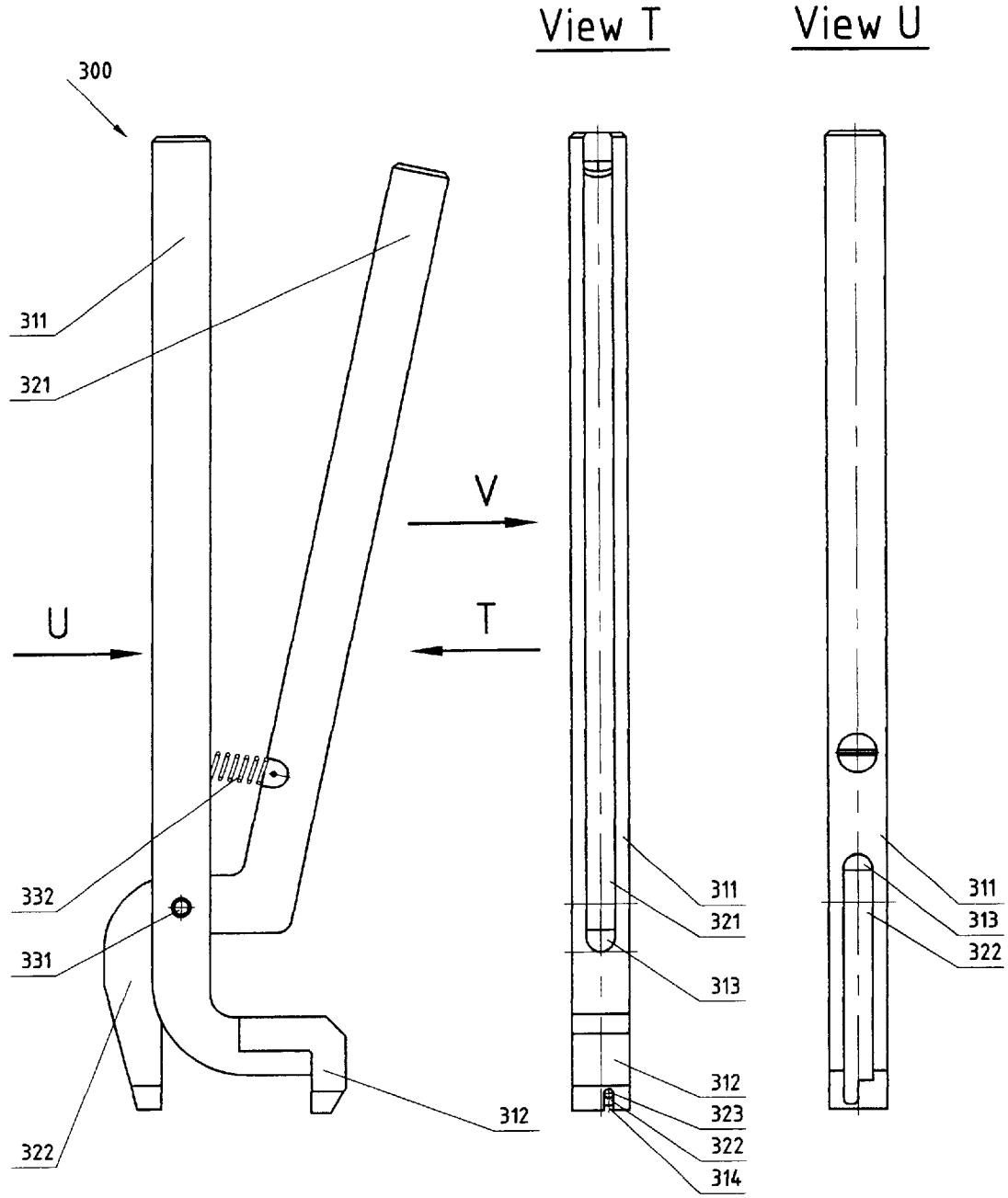

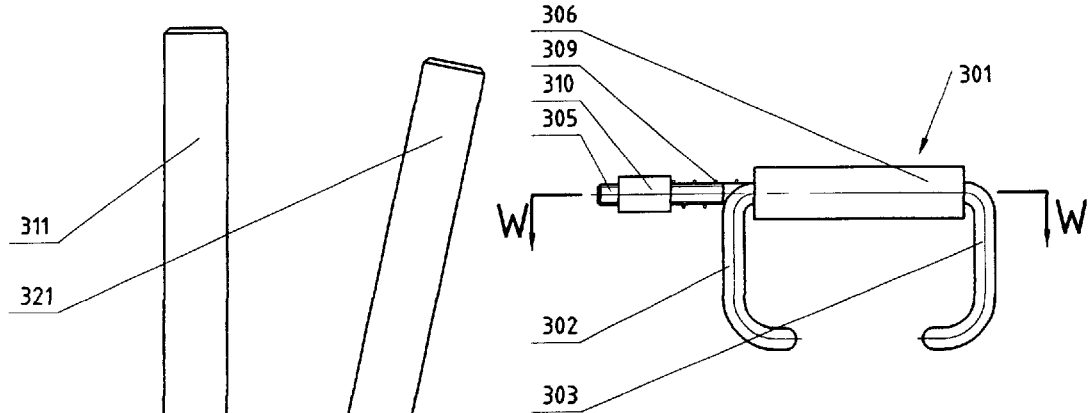
Fig. 30
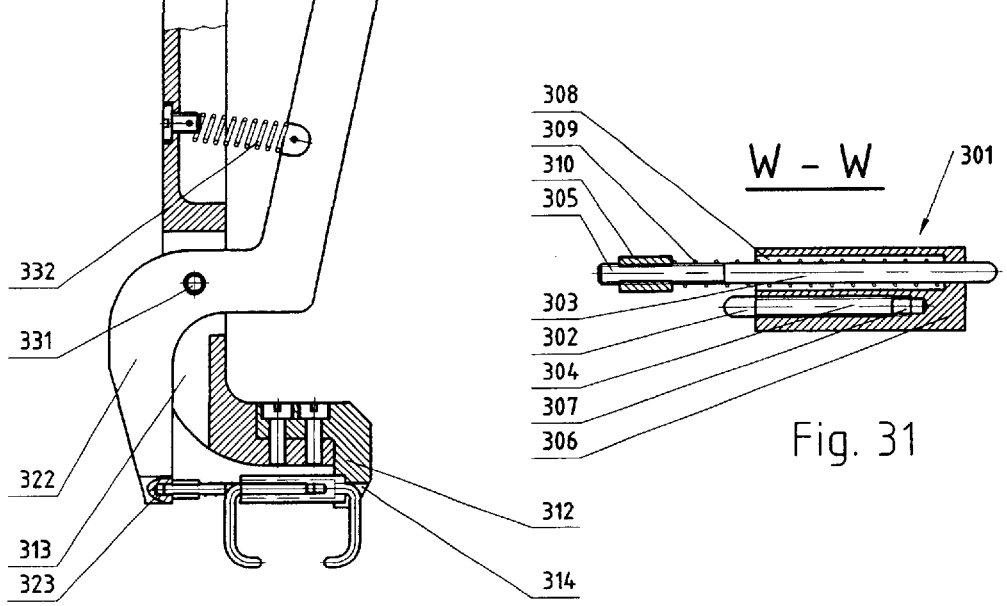
Fig. 31
Fig. 29

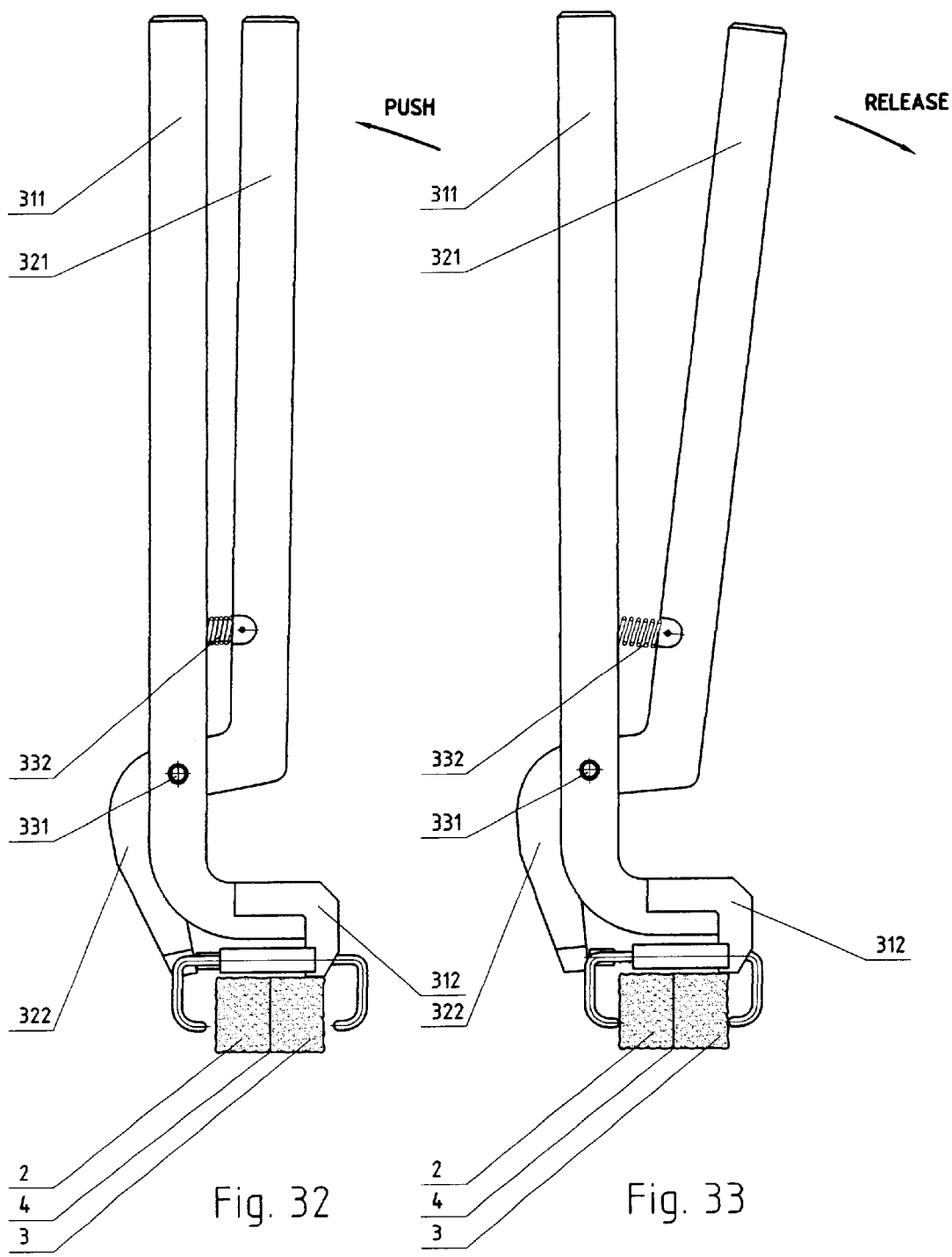

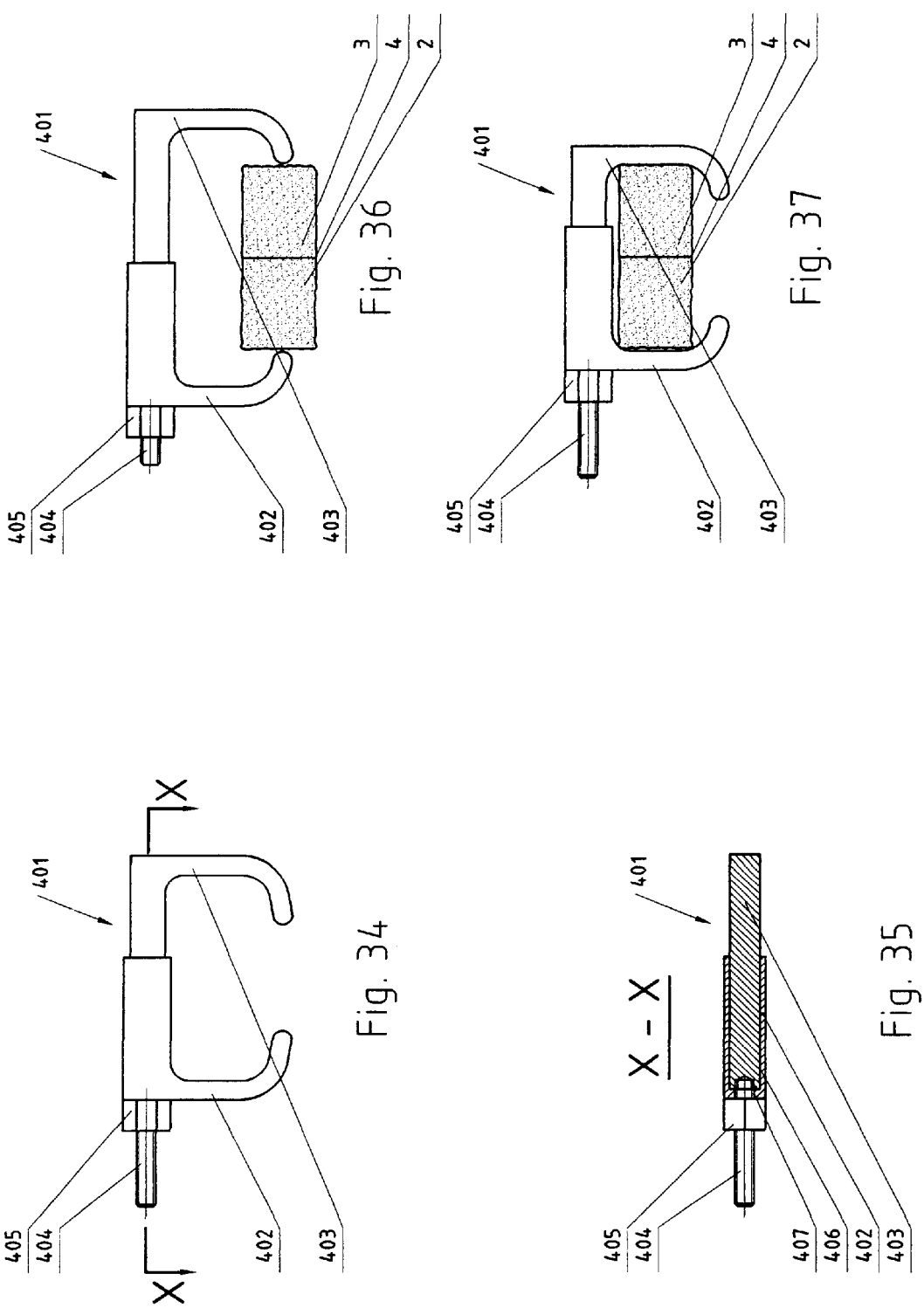

STRERNUM CLOSURE DEVICE AND PINCERS FOR MOUNTING STAPLES AND APPROXIMATOR BRACKETS

CROSS-REFERENCE TO RELATED APPLICATIONS

This Application is a Continuation-In-Part of co-pending application Ser. No. 09/799,475 filed Mar. 5, 2001, which is a Continuation-In-Part of co-pending application Ser. No. 09/626,802 filed Jul. 27, 2000, both of which are hereby incorporated by reference specifically for disclosure on the sternum closure device and in general, in its entirety.

FIELD OF THE INVENTION

The present invention relates to medical devices for closure of a severed sternum and pincers for mounting staples and special staples. In particular, the invention is directed to a sternum closure assemblies and methods for re-approximating split portions of tissue to retain the split portions in adjacent contacting relation to promote healing thereof. Additionally, the invention is directed to specially designed pincers which are used to bring the two halves of the sternum and holds them firmly together without movement so that the stapler can be used accurately.

BACKGROUND OF THE INVENTION

During surgery that involves a median sternotomy, for example, open-heart surgery, the sternum is cut longitudinally to allow access to the organs within the thoracic cavity. A partial or median sternotomy is a procedure by which a saw or other approximate cutting instrument is used to make a midline, longitudinal incision along a portion or the entire axial length of the patient's sternum, allowing two opposing sternal valves to be separated laterally. Upon completion of the surgery, the sternum is rejoined and closed securely.

Traditionally, the sternal halves have been closed with stainless steel wires which are wrapped around or through the sternal halves to engage in face-to-face relationship and compressed together while the sternum heals. For example, in one version, a surgical needle with the metal wire is led via both split portions of a severed sternum and the free metal wire is cut-off. In another version, the wire tips are further led via openings in special staples, to project outside and the tips are twisted together by tightening the suture, U.S. Pat. No. 4,512,346 and U.S. Pat. No. 5,849,012. However, these devices have certain shortcomings, in that they require significant force, are difficult to maneuver and the sharp wire edges sometimes cause injury and eventually, infection to soft tissues.

Other prior art sternum closure assemblies include one or two metal plates, these plates being provided with rows of openings, through which extend the screws, pins, or metal wire, to bring together the severed portions of the sternum. U.S. Pat. No. 4,585,341. These devices have drawbacks in that they are ineffective in fixing the split portions of the severed sternum. Moreover, they are foreign bodies in the thoracic cavity, and they can cause disturbance in blood supply to the osseous tissue, thereby prolonging healing and increasing chances of infection.

The strap assemblies known heretofore incorporate clamps, clasps, bands, strips with or without openings and complex locking mechanisms. U.S. Pat. Nos. 5,356,417; 5,462,542; and 6,007,538. The use of compression presents problems for blood circulation and soft tissues. Other versions of sternum closure devices use tongs, plugs or guns with anvils, to apply staples through the osseous tissue of the sternum. U.S. Pat. Nos. 4,122,989; and 4,481,960. However, these devices suffer from several drawbacks, for example, significant force is required to puncture the osseous tissue and insert a staple. In addition, these prior art devices are imprecise in positioning the staples, and do not permit the anvil to bend the staple through 180° angle. Finally, the devices are cumbersome and cause shaking of the organs in the thoraxic cavity.

A certain amount of emphasis has also been directed towards the use appropriate staples which minimize healing time, minimize distortion of the material stapled, minimize damage of material stapled, minimize scar tissue formation and achieve uniform compression of stapled material. U.S. Pat. Nos. 5,342,396 and 5,667,527. However, these devices suffer from several of the same drawbacks discussed above for earlier models of the sternum closure devices and systems.

It would accordingly be desirable to provide a sternum closure device which is stable in construction and effectively secures the severed portions of sternum or other tissue together, i.e., secures the staples in well defined locations, at a predetermined angle, and at a desirable tension to promote uniform healing of the tissue portions while avoiding complications associated with tissue injury, infection and compression. It would also be desirable to provide an instrument which can bring the two halves of the sternum and holds them firmly together without movement so that the stapler can be used accurately.

The two halves of the severed sternum have to be held firmly in place while the stapling process is being performed. Therefore the present sternal approximating bracket has been invented to perform this process quickly and more strongly than previous inventions. It is suggested that 3 of these sternal approximating brackets are placed so as to hold the two halves of the sternum firmly.

SUMMARY OF THE INVENTION

The present invention provides improved devices and methods of joining with staples, the opposite portions of a severed sternum following a median or partial sternotomy that overcomes the above cited problems inherent in previous sternum closure devices. Generally, the present invention is embodied in an anvil for bending the staples, a bracket positioned opposite the anvil, a means for making openings in the tissue, and a means for feeding and mounting the staples.

According to a first aspect of the invention, a sternum closure device comprises an anvil having an element comprising two slots, said element being used for bending the staples with precision in a specific angular range up to 180°. A bracket is provided with an additional slot to guide the drilling means and to mount the staples in the sternum. Other improvements to the anvil and bracket include bending elements which facilitate their mounting on the sternum portions. The bracket is provided with a post and a lock, the post having two mutually perpendicular openings and a pin mounted on it, and the lock comprising a housing with a slot, and a spring-actuated locking element with a handle situated in the slot.

According to a second aspect of the invention, the bracket is joined with the anvil through a spring-actuated screw having a handle, said screw being positioned in a threaded opening located in the bracket. Two guides are situated between the anvil and the bracket and parallel to the screw, said guides being installed in the openings of the bracket to facilitate displacement of the bracket with respect to the anvil.

The sternum closure device of the present invention comprises a bit brace with a gear and two chucks having interchangeable drills for simultaneously drilling openings in both portions of a severed sternum. The gear includes a housing, said housing including a basis with a lug, and a cover. The lug is provided with an opening and a slot. A drive gear wheel is installed on a driving shaft, said driving shaft being joined with a pneumatic drive. Two drive gear wheels are in engagement with the drive wheel gear. The drive wheel is fastened on the drive shafts and the chucks with interchangeable drills are installed on these drive shafts.

According to another aspect of the invention, the sternum closure device comprises a means for feeding and mounting the staples, including a carrying element constructed of a bed, said bed having a first and second surface. Two ribs provided with a positive stopper are situated perpendicularly to the bed surface. The bed surface and each rib are provided with slots. The first bed surface is also provided with a lug having a threaded opening and a locking screw. The second and opposite bed surface is designed as a wall having a handle. A sub-assembly used for mounting the staples, is installed on the bed surface, said sub-assembly comprising an L-shaped lever and two spring-actuated posts. Said L-shaped lever has a shaft side and a long side. The two spring-actuated posts are locked on the bed surface and passed through the openings in the shaft side of the L-shape lever. The long side of the L-shaped lever is placed in the slot of the bed surface.

A cartridge is placed between the bed ribs, said ribs having an internal side and an external side. The cartridge comprises slots for the staples and a spring-wise element situated between the cartridge and the face wall of the bed. The spring-wise element presses the cartridge with staples against a plurality of stoppers installed on the internal side of the bed ribs.

According to a preferred embodiment of the invention, an instrument for drilling openings is installed on the bracket post along with precise and well-controlled means for feeding and mounting staples. A compression spring is situated between the instrument for drilling openings and the means for feeding and mounting staples. The instrument for drilling opening may be displaced from the bracket post when necessary.

According to yet another preferred embodiment of the invention, especially designed pincers for mounting staples into the severed sternum are provided. These pincers bring the two halves of the sternum and holds them firmly together without movement so that the stapler can be used accurately. These pincers are not bulky nor do they interfere with the use of the stapler and application of the staples.

The sternum closure device of the present invention comprises a clamping mechanism installed on the bracket providing reciprocating displacement along the bracket, and consisting of a carrying element, an assembly for mounting the staples, a cartridge containing the staples, and a lock fixing the clamping mechanism on the bracket. The assembly, the cartridge, and the lock are fastened on the carrying element. The carrying element is provided with two guide-openings for drilling openings in the parts of the severed sternum by one of any drilling instrument which is used in sternal surgery.

According to another aspect of the invention, the sternum closure device comprises a carrying element constructed of a bed, having a rib provided with a cut and situated perpendicularly to the bed. The assembly for mounting the staples, constructing as a pressure mechanism comprises a pusher with a transmitting element and spring-wise element. The transmitting element being fastened to the pusher. The cartridge is fastened on the bed and comprises a holder of the staples and means for feeding of the staples. The means contains a pressure element is placed inside the holder. The pressure element comprises a handle and spring-wise element. The lock is fastened on the bed and is constructed as a housing comprising a locking element with a handle and spring-wise element. The locking element and the spring-wise element are placed inside the housing.

In the present invention, the two halves of the severed sternum have to be held firmly in place while the stapling process is being performed. Therefore the present sternal approximating bracket has been invented to perform this process quickly and more strongly than previous inventions. It is suggested that 3 of these sternal approximating brackets are placed so as to hold the two halves of the sternum firmly.

The advantages of these sternal approximating brackets is that: a) they have a low profile and so do not interfere with the smooth performance of the stapling process, b) if compression fixation of the sternum is anticipated (this is an accepted method of external fixation in the treatment of various orthopedic fractures), this sternal approximating bracket can be inserted through the intact skin so as to compress the two halves of the severed sternum and left in place until union has been achieved.

BRIEF DESCRIPTION OF THE DRAWINGS

A more complete understanding of the present invention and the attendant advantages and features thereof will be more readily understood by reference to the following detailed description when considered in conjunction with the accompanying drawings wherein:

FIG. 11 is a sectional view in the plane of line D—D of a displacement mechanism, which is shown in FIG. 1.

FIG. 12 is a view following detail I, which is shown in FIG. 7.

FIG. 13 is a sectional view of the sternum closure device, which is shown in FIG. 8, in the plane of line H—H.

FIG. 14 is a sectional view of the sternum closure device, which is shown in FIG. 9, in the plane of line K—K.

FIG. 26 is a side view of the pincers for mounting staples.

FIG. 27 is a butt view of the pincers for mounting staples, taken in the plane of arrow A of FIG. 16.

FIG. 28 is a butt view of the pincers for mounting staples, taken in the plane of arrow B of FIG. 16.

FIG. 29 is a side view of the pincers with special staple, taken in the plane of arrow C of FIG. 17.

FIG. 30 is a side view of the special staple, which is shown in FIG. 19.

FIG. 31 is a sectional view of the special staple, which is shown in FIG. 20 in the plane of line D—D.

FIG. 32 is a side view of the pincers with special staple before setting of the special staple on the severed sternum.

FIG. 33 is a side view of the pincers with special staple after setting of the special staple on the severed sternum.

FIG. 34 is a side view of the sternal approximator bracket.

FIG. 35 is a sectional view of the sternal approximator bracket, which is shown in FIG. 34 in the plane of line X—X.

FIG. 36 is a side view of the sternal approximator bracket before setting of the sternal approximator bracket on the severed sternum FIG. 37 is a side view of the sternal approximator bracket after setting of the sternal approximator bracket on the severed sternum.

DETAILED DESCRIPTION OF THE PREFERRED EMBODIMENT

Figure 1:
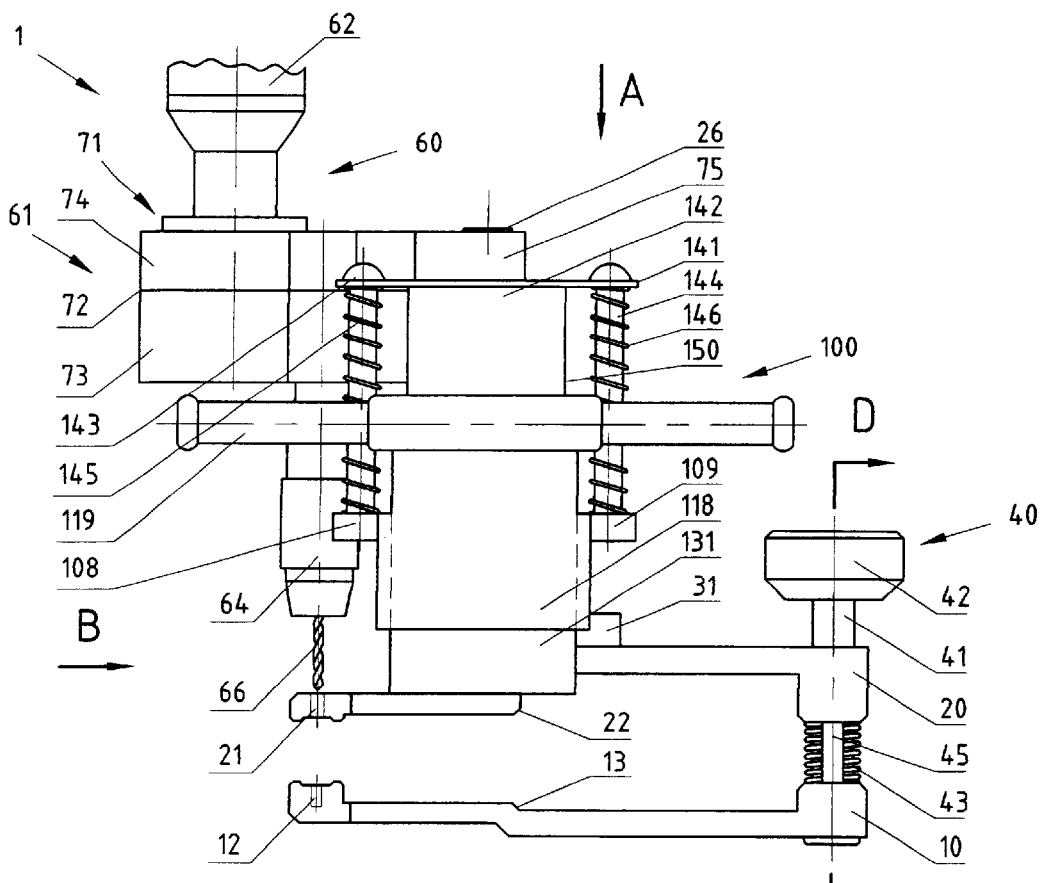
FIG. 1 is a side view of a sternum closure device positioned in the state of drilling openings in the sternum.
Figure 2:
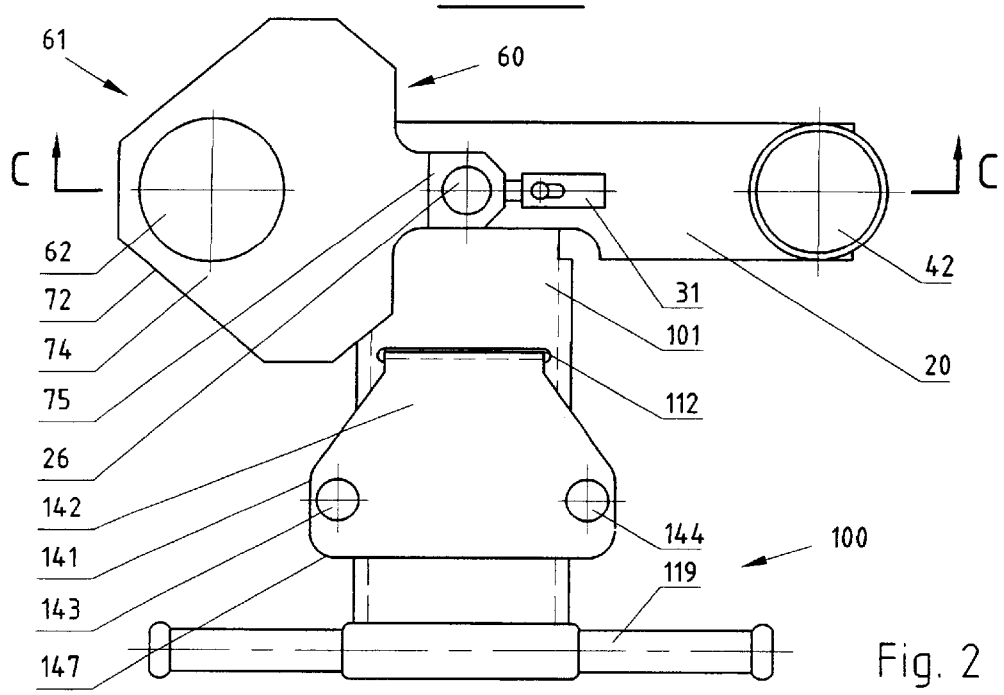
FIG. 2 is a top view of the sternum closure device, taken in the plane of FIG. 1.
Figure 3:
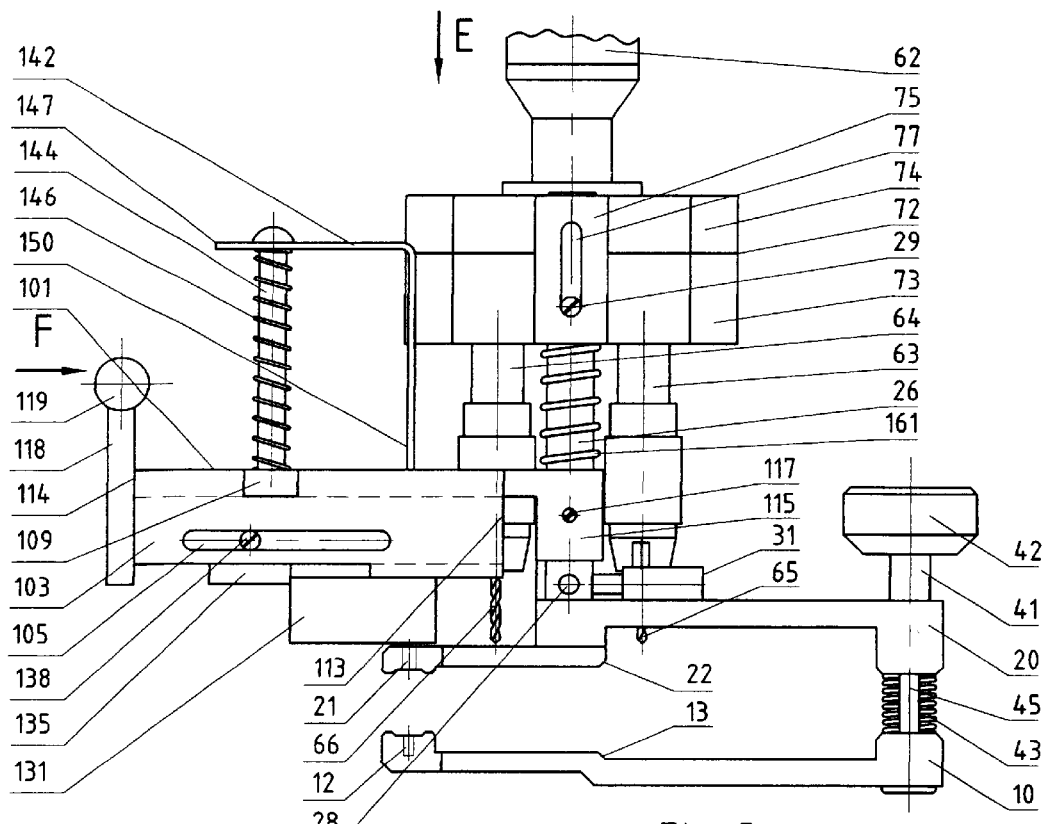
FIG. 3 is a side view of the sternum closure device when it is in the state of mounting staples.
Figure 4:
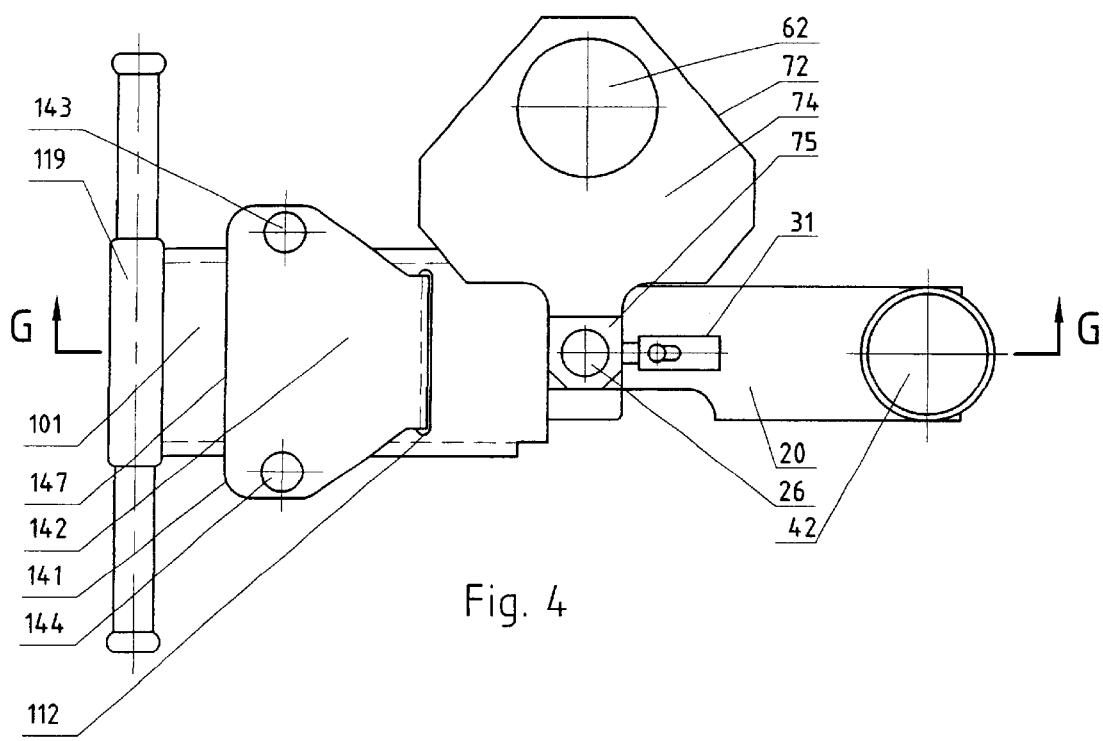
FIG. 4 is a top view of the sternum closure device, taken in the plane of arrow E. of FIG. 3

According to yet another preferred embodiment of the invention, especially designed pincers for mounting staples into the severed sternum are provided. These pincers bring the two halves of the sternum and holds them firmly together without movement so that the stapler can be used accurately. These pincers are not bulky nor do they interfere with the use of the stapler and application of the staples.

The sternum closure device of the present invention comprises a clamping mechanism installed on the bracket providing reciprocating displacement its along of the bracket, and consisting of a carrying element, an assembly for mounting the staples, a cartridge containing the staples, and a lock fixing the clamping mechanism on the bracket. The assembly, the cartridge, and the lock are fastened on the carrying element. The carrying element is provided with two guide-openings for drilling openings in the parts of the severed sternum by one of any drilling instrument are in use in sternal surgery.

According to another aspect of the invention, the sternum closure device comprises a carrying element constructed of a bed, having a rib provided with a cut and situated perpendicularly to the bed. The assembly for mounting the staples, constructing as a pressure mechanism comprises a pusher with a transmitting element and spring-wise element. The transmitting element being fastened to the pusher. The cartridge is fastened on the bed and comprises a holder of the staples and means for feeding of the staples. The means contains a pressure element is placed inside the holder. The pressure element comprises a handle and spring-wise element. The lock is fastened on the bed and is constructed as a housing comprising a locking element with a handle and spring-wise element. The locking element and the spring-wise element are placed inside the housing.

Referring to FIGS. 1 to 13, a sternum disclosure device 1 is shown to provide a system and method for joining two portions 2 and 3, of a severed sternum 4, by means of staples 5, having legs 6 and 7, which are inserted through openings 8 and 9 of the severed sternum 4.

A preferred embodiment of the sternum closure device includes an anvil for bending staples. This anvil is positioned on the internal side of the severed sternum. A bracket is situated on the outer side of the severed sternum, opposite the anvil. The anvil comprises an element for bending the staples. It is designed to have two slots. In addition, the bracket has a third slot which is intended to be guide for the drills and for mounting the staples on the sternum. The unique feature about the present invention is that the anvil and the bracket are designed with bends such that these bends facilitate their proper mounting on the sternum.

The bracket is also provided with a rotatable post and a lock. The post is provided with two mutually perpendicular openings and a pin. The lock comprises of a housing with a slot. A spring-actuated locking element having a handle is situated in the slot in the lock housing.

Referring to FIG. 1, the sternum device 1 comprises of an anvil 10 and a bracket 20, said anvil and said bracket being joined together by a displacement means 40. The sternum device 1 further comprises of an instrument 60 which is provided to form openings in the sternum, and a staple feeding means 100, which is used for feeding and mounting the staples.

Figure 9:
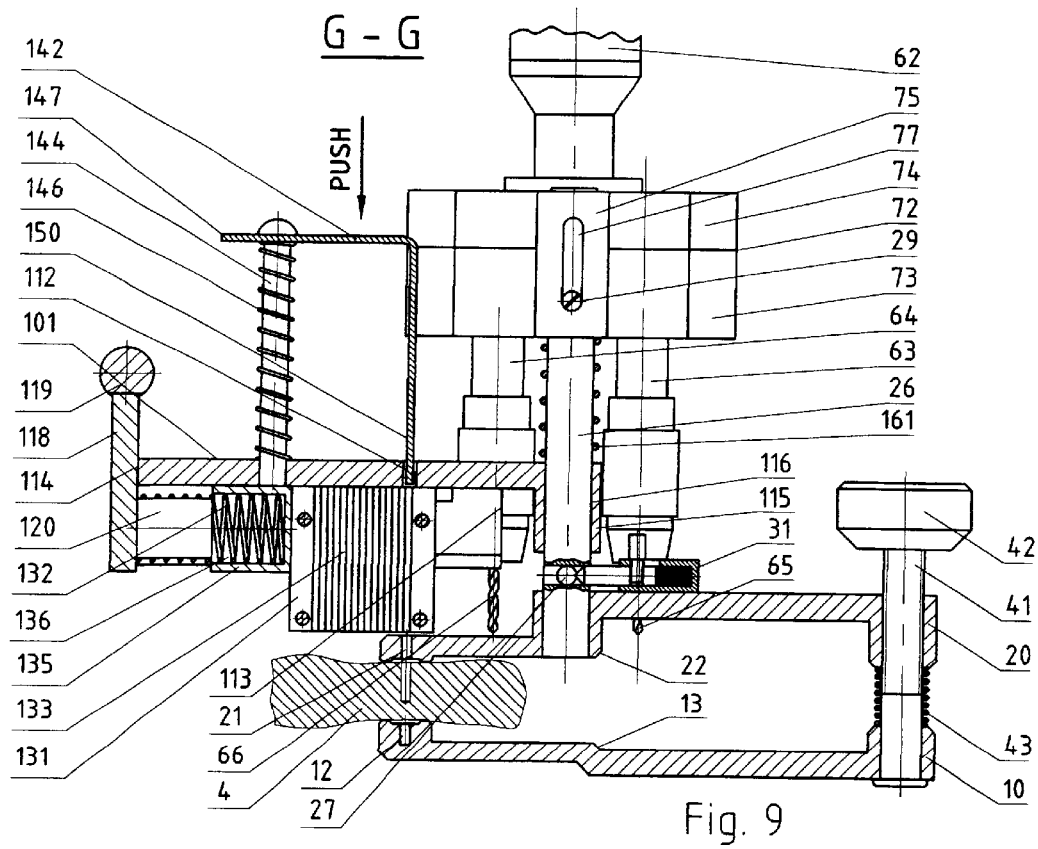
FIG. 9 is a sectional view of the sternum closure device, which is shown in FIG. 4, in the plane of line G—G; this device is in the state preceding mounting the staples in the sternum.

Referring to FIGS. 1 and 9, anvil 10 is provided with two slots 11 and 12 for the purpose of bending staples 5, a bend 13 and a through opening 14 used for joining the displacement means 40. The bracket 20 comprises of a through slot, a bend 22 and a threaded opening 23, said opening 23 serving to attach the displacement means 40. The bracket 20 further comprises of two through openings 24 and 25, and a cylindrical post 26. The cylindrical post 26 is installed on bracket 20 to provide a turning means, the cylindrical post being further provided with two openings 27 and 28, and a pin 39. A lock 31 is installed traversally to cylindrical post 26 and the lock 31 is fastened on bracket 20.

The bracket is joined to the anvil through a displacement mechanism. This mechanism provides reciprocating displacement of the bracket with respect to the anvil. The displacement mechanism comprises of a spring-actuated screw with a handle. This screw is positioned in the threaded opening in the bracket where it is attached to the anvil. Two guides are situated between the anvil and the bracket. These guides are parallel to the screw and are locked in the anvil. The guides are installed in the through openings of the bracket to enable its displacement in the direction of the guides.

Referring to FIGS. 1 and 9, the anvil 10 and bracket 20 are joined via the displacement means 40 to enable reciprocating displacement of bracket 20 to and from the anvil 10. The displacement means comprises of screw 41, said screw extending into a handle 42, a compression spring 43 and two guides 44 and 45. The screw 41 is fastened through a threaded opening 23 in bracket 20, and is locked rotatably in the opening 14 of anvil 10. A spring 43 is installed between the anvil 10 and the bracket 20, in line with the screw 41. Guides 44 and 45 are locked onto the anvil 10 and are in a parallel position to screw 41. Guides 44 and 45 are installed in such a way through openings 24 and 25 of bracket 20 to enable displacement of bracket 20 along guides 44 and 45.

Figure 10:
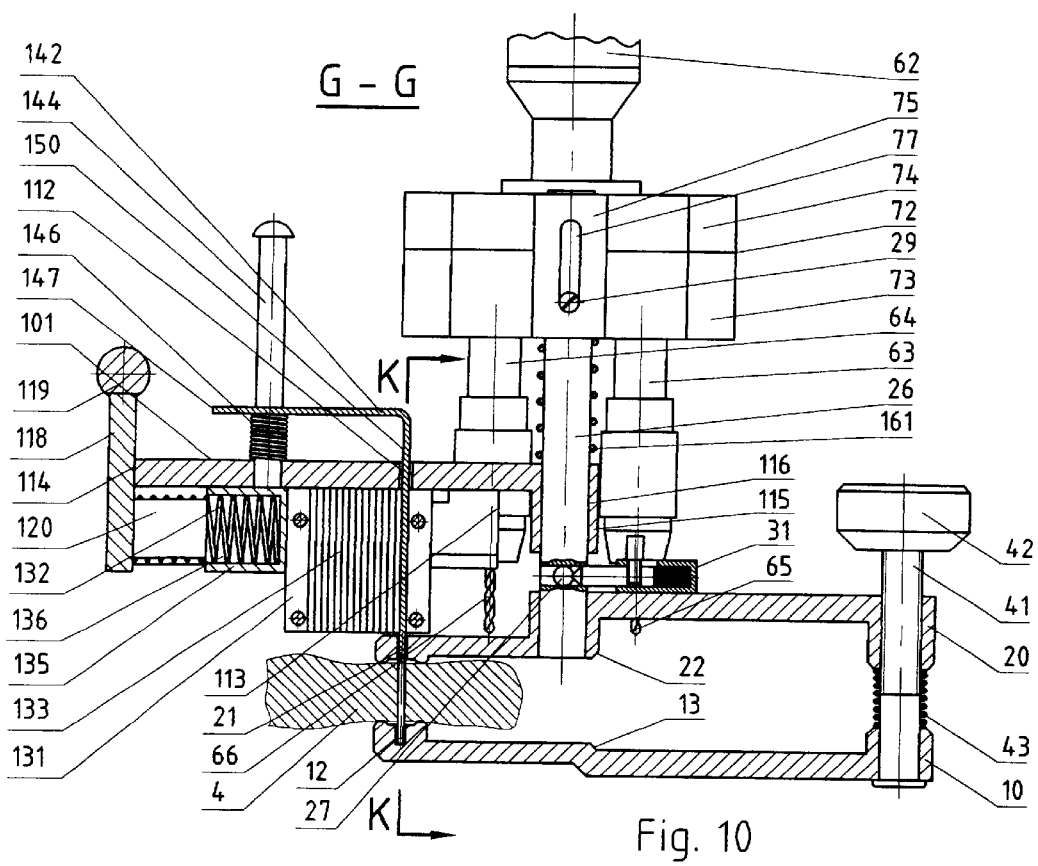
FIG. 10 is a sectional view of the sternum closure device, which is shown in FIG. 4, I the plane of line G—G; this device is in the process of mounting the staples.

Referring to FIG. 10, lock 31 comprises of housing 32, a locking element 33, a spring 34 and a handle 35. The locking element 33 and the spring 34 are introduced partially into housing 32, and the locking element 33 is presented from dropping out by the handle 35, said handle 35 being installed in a slot 36 located in the housing 32.

In a preferred embodiment of the sternum closure device, the instrument for formation of openings in the sternum is constructed as a hand bit brace, a pneumatic bit brace, a laser perforator or an ultra-sound perforator. The bit brace comprises of a gear and two chucks. These chucks have interchangeable drills for simultaneously drilling openings in both portions of the severed sternum, which are to be attached.

The gear consists of a housing. The housing includes a basis with a lug and a cover. The lug is provided with a through opening and a slot. A plurality drive of gear wheels each installed on a driving shaft. The driving shaft is then joined to a pneumatic drive. Chucks with interchangeable drills are also installed on the drive shafts.

Referring to FIGS. 1, 2, 5, 7 and 8, an instrument 60 is provided for formation of openings. The instrument is constructed as a bit brace 61 with a pneumatic drive 62 and two chucks 63 and 64. The two chucks are provided for mounting interchangeable drills 65 and 66. The instrument 60 further comprises a gear 71. Gear 71 is installed over housing 72, said housing comprising of a basis 73 and a cover 74. Base 73 is provided with lug 75, said lug 75 having an opening 76 and a slot 77. A driving gearwheel is arranged in the internal space of housing 72, and installed on a driving shaft 79. The driving shaft 79 is mounted on base 73 of housing 72 by means of bearings 86, 87, 88 and 89. The driving shaft 79 is further completed with the pneumatic drive 62, said drive being designed as a pneumatic motor. Chucks 63 and 64 are installed on driving shafts 84 and 85 and these chucks are used for mounting the interchangeable drills 65 and 66.

Instrument 60 and pin 29 are installed on cylindrical post 26 to enable displacement along the cylindrical post 26. The pin 29 is locked on cylindrical post 26 via slot 77 of lug 75 of gear 71. Thus, pin 29 limits the magnitude of instrument 60 and prevents its turning around post 26.

A portable means of feeding and mounting the staples is constructed as a bed with two ribs situated perpendicularly to the bed surface. The ribs are provided with a positive stopper. The bed surface and each rib are provided with through slots. One bed surface is provided with a lug, the lug having a threaded through opening and a locking screw in it. The other bed surface is designed as a wall with a handle.

Referring to FIGS. 3,4, 6, 9,10 and 14, a feeding and staple mounting means 100 comprises of a carrying element constructed as bed 101 having two ribs 102 and 103. These ribs are perpendicular to bed 101 and each rib is provided with longitudinal slots 104 and 105. Stoppers 106 and 107 are installed on the internal side of each rib 102 and 103, respectively. Bed 101 is provided with two lugs 108 and 109, said lugs in turn are provided with openings 110 and 111 respectively. Bed 101 is further provided with slot 112, said slot 112 being placed in parallel to sides 113 and 114 of bed 101. Side 113 is provided with lug 115, which in turn has an opening 116 and a locking screw 117 fastened to the opening 116. Wall 118, having an internal side and an external side, is situated in perpendicular to bed 101 on side 114. Handle 119 is locked to wall 118. A cylindrical support 120 is further installed on the internal side of wall 118.

Feeding means 100 further comprises of a cartridge 131 which is positioned between ribs 102 and 103 of bed 101, and a spring 132. Cartridge 131 is designed as a parallel component having slots 133 used for positioning the staples 5. A bracket 135 having an opening 136 is positioned on face side 134 of cartridge 131. Cartridge 131 is installed between ribs 102 and 103 and is held inside the bed 101 by two pins 137 and 138. These two pins are positioned in slots 104 and 105 of ribs 102 and 103 respectively. Spring 132 is arranged in a cylindrical support 120 of wall 118. It is further inserted partially in opening 136 of bracket 135.

Feeding means 100 further comprises subassembly 141, used for mounting the staples. The subassembly 141 comprises a pressure L-shaped lever 142, two posts 143 and 144, and two springs 145 and 146. The L-shaped lever 142 has a short side 147, the short side 147 having two openings 148 and 149. Posts 143 and 144 pass through openings 148 and 149 respectively. Springs 145 and 146 are installed singly on posts 143 and 144 respectively. The subassembly 141 is installed on bed 101. The L-shaped lever has a long side 150, which is introduced in slot 112. Posts 143 and 144 and springs 145 and 146 are locked through openings 110 and 111 of lugs 108 and 109, respectively.

Staple feeding means 100 is mounted on post 26 and instrument 60 and locked in place by a screw 117. In addition, spring 161 is installed on feeding means 100 and instrument 60.

Operation of the Sternum Closure Device

The mode of operation of the sternum closure device is described herein below.

The bracket 20 is moved progressively in direction away from anvil 10 by the displacement mechanism 40 (see FIG. 11). The screw 41 is rotated by handle 42, for example, in an anti-clockwise direction. Bracket 20 moves progressively along guides 44 and 45 in direction away from anvil 10 with releasing spring 43. This results in greater distance between anvil 10 and bracket 20. Anvil 10 and bracket 20 are positioned correspondingly from the internal and external sides of portion 2 and 3 of the severed sternum 4.

Bend 13 of anvil 10 and bend 22 of bracket 20 facilitate mounting anvil 10 and bracket 20 on sternum 4.

With rotation of screw 41 by handle 42 in the opposite direction (in this case—in the clock-wise direction), bracket 20 moves progressively along guides 44 and 45 towards anvil 10. This motion is accompanied with compression of spring 43 and decrease of the distance between anvil 10 and bracket 20 in reference to the internal and external portions 2 and 3 respectively, of the severed sternum 4.

The sternum closure device 1 is arranged in the position of drilling openings in portions 2 and 3 of the severed sternum 4 (FIGS. 1, 2, 5, 7) by lock 31 (FIG. 12).

In the initial state spring 34 of lock 31 is released and the locking element 33 is placed in one of two mutually perpendicular through openings 27 or 28 of post 26 of bracket 20. As displacement handle 35 moves along slot 36, the locking element 33 is removed from the corresponding openings 27 or 28 of post 26 by compression of spring 34. Then post 26 is released from locking and it turns in bracket 20 until the axis of the through opening 27 is aligned with the axis of the locking element 33 of lock 31. With descending handle 35 the compressed spring 34 pushes out the locking element 33 from housing 32. The locking element is introduced in such a way into the through opening 27 of the post 26, that it fixes in a position of the drilling openings.

Figure 7:
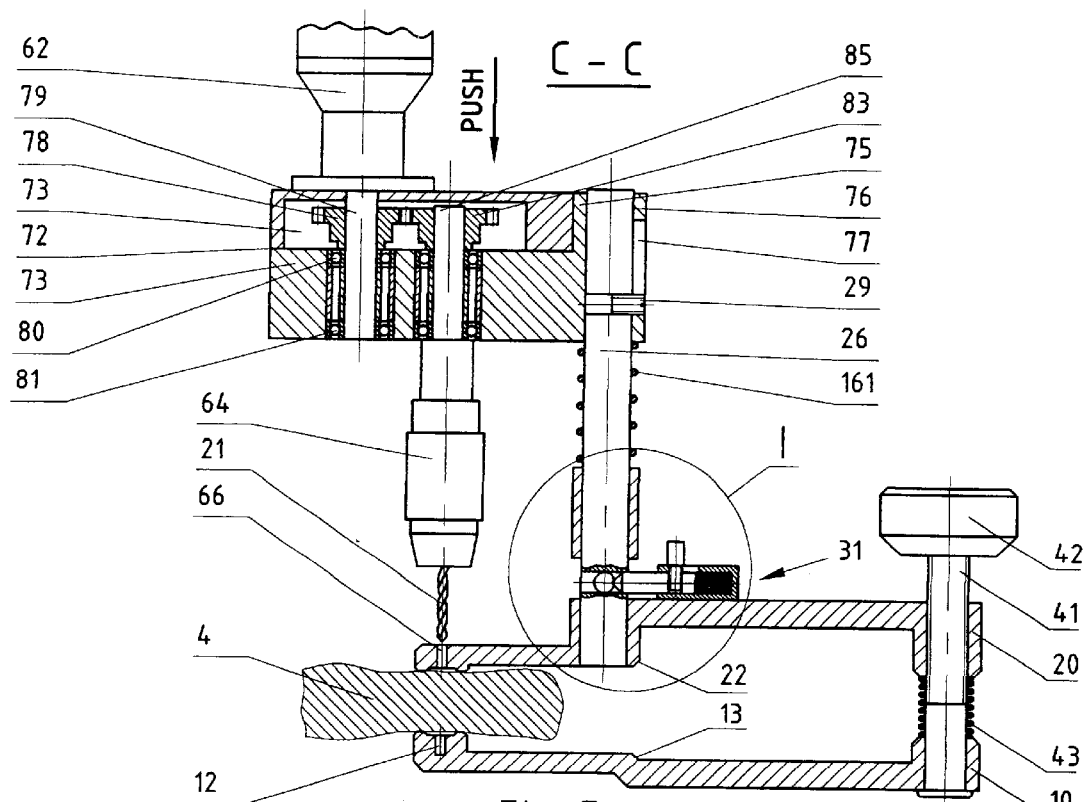
FIG. 7 is a sectional view of the sternum closure device, which is shown in FIG. 2, in the plane of line C—C; this device is in the state preceding drilling the openings in the sternum.
Figure 8:
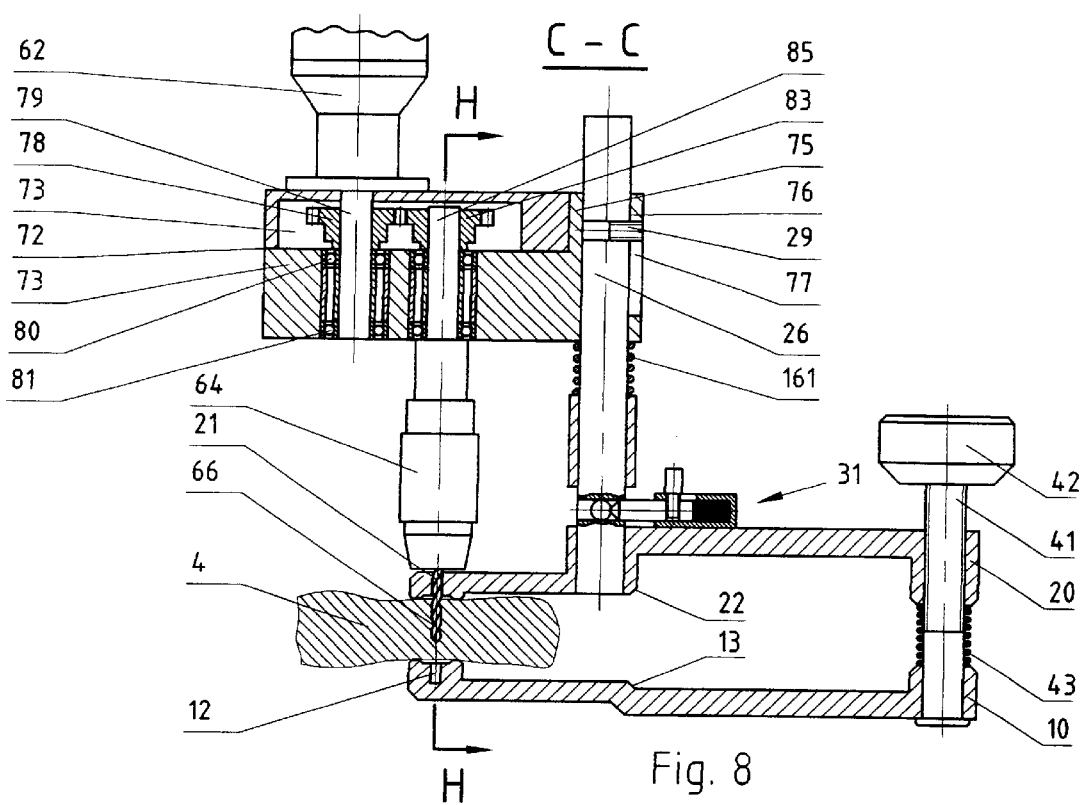
FIG. 8 is a sectional view of the sternum closure device, which is shown in FIG. 2, in the plane of line C—C; this device is in the process of drilling the openings in the sternum.

Drilling openings 8 and 9 are performed in portions 2 and 3 of the severed sternum 4 (FIGS. 7, 8) by instrument 60 intended for drilling openings. This instrument is installed on post 26 of bracket 20 to allow its reciprocating motion along post 26. Then the pneumatic motor 62 is switched on. The motor via the drive gear wheel 78 and two driven gear wheels 82 and 83 of gear 71 causes two chucks 63 and 64 to rotate with drills 65 and 66 respectively (FIG. 7). By pushing in direction of arrow PUSH onto cover 74 of gear 71 of instrument 60, the bit brace 61 is displaced along post 26 of bracket 20 toward anvil 10. This displacement is accompanied by compression of spring 161 and drills 65 and 66, which pass via slot 21 of bracket 20. Openings 8 and 9 are drilled simultaneously correspond to two portions 2 and 3 of the severed sternum 4 (FIGS. 8, 13). The magnitude of displacement of instrument 60 along post 26 is limited by the length of slot 77 and the limiting pin 29 (FIGS. 8, 13). With completion of drilling opening 8 and 9 (see FIG. 13), compression on instrument 60 is stopped. It returns to its initial position by release of spring 161 (see FIG. 8).

Then the sternum closure device 1 is transferred in the state of mounting staples 5 in sternum 4 (FIGS. 3, 4, 6, 9) by lock 31 (FIG. 12). With displacement of handle 35 of lock 31 along slot 36, the locking element 36 is removed from the through opening 27 of post 26, and compresses spring 34. Then post 26 is released and it is turned in bracket 20 until the axis of the through opening 28 is aligned with the axis of the locking element 33 of lock 31. With descending handle 35 the compressed spring 34 pushes out the locking element 33 from housing 32. Then this locking element is introduced into the through opening 28 of post 36 fixings in such a way that it facilitates mounting of the staples.

Mounting staples 5 in the through openings 8 and 9 in respective portions 2 and 3 of the severed sternum 4 (see FIGS. 9, 10) is performed by mechanism 100 of feeding and mounting staples. This is accomplished by locking mechanism 100 on post 26 of bracket 20. Cartridge 131 is filled by staples 5 through slots 133. When mounting the staples, the locking mechanism is set above the through slot 21 of bracket 20. Cartridge 131 with staples 5 are forced from Cartridge 131 onto stoppers 106 and 107 by spring 132 (FIG. 10). While pushing in direction of arrow PUSH on the short side 137 of the L-shaped lever 142, the cartridge is displaced along two posts 143 and 144 towards anvil 10. This is accompanied by compression of springs 145 and 146. The long side 150 of the L-shaped lever 142 passes via the through slot 112 and presses out the first staple 5 from the through slot 133 of cartridge 131. This staple is introduced in turn via the through slot 21 of bracket 20 by its two legs 6 and 7 corresponding to openings 8 and 9 in portions 2 and 3 respectively, of the severed sternum 4. With further pushing on the short side 147 of the L-shaped lever 142, legs 6 and 7 of staple 5 pass via openings 8 and 9. The form of legs 6 and 7 is changed with bending because of slots 11 and 12 of anvil 10, while pulling together portions 2 and 3 of the severed sternum 4 (FIGS. 10, 14).

The angle in which the two legs of the staple bend is circular and effectively secures the two divided portions of the sternum in a stable grip. The present invention is directed to a sternum closure device which securably retains a plurality of staples around sternum portions to maintain the portions in adjacent engaged relation during healing. The present invention minimizes damage of a tissue stapled and prevents formation of scar tissue.

After mounting of staple 5 is completed the compression (FIG. 5), on lever 142 is terminated. It returns to its initial position owing to release of springs 145 and 146 (FIG. 9). After egress of the long side 150 of L-shaped lever from the through slot 133 of cartridge 131, spring 131 is released. The cartridge 131 is displaced through one further step until the next staple 5 is arranged in through slot 133, with stoppers 106 and 107 (FIGS. 9,14). In order to mount additional staple 5, bracket 20 is displaced progressively away from anvil 10 by the displacement mechanism 40 (FIG. 11). Rotation of screw 41 by handle 42 in an anti-clock wise direction allows displacement of bracket 20 progressively along guides 44 and 45 toward anvil 10. This release spring 43 and enlarges the distance between anvil 10 and bracket 20.

Then the sternum closure device 1 is made ready for mounting the next staple 5. This process of mounting displacing and compressing staple 5 is repeated as necessary.

Figure 15:
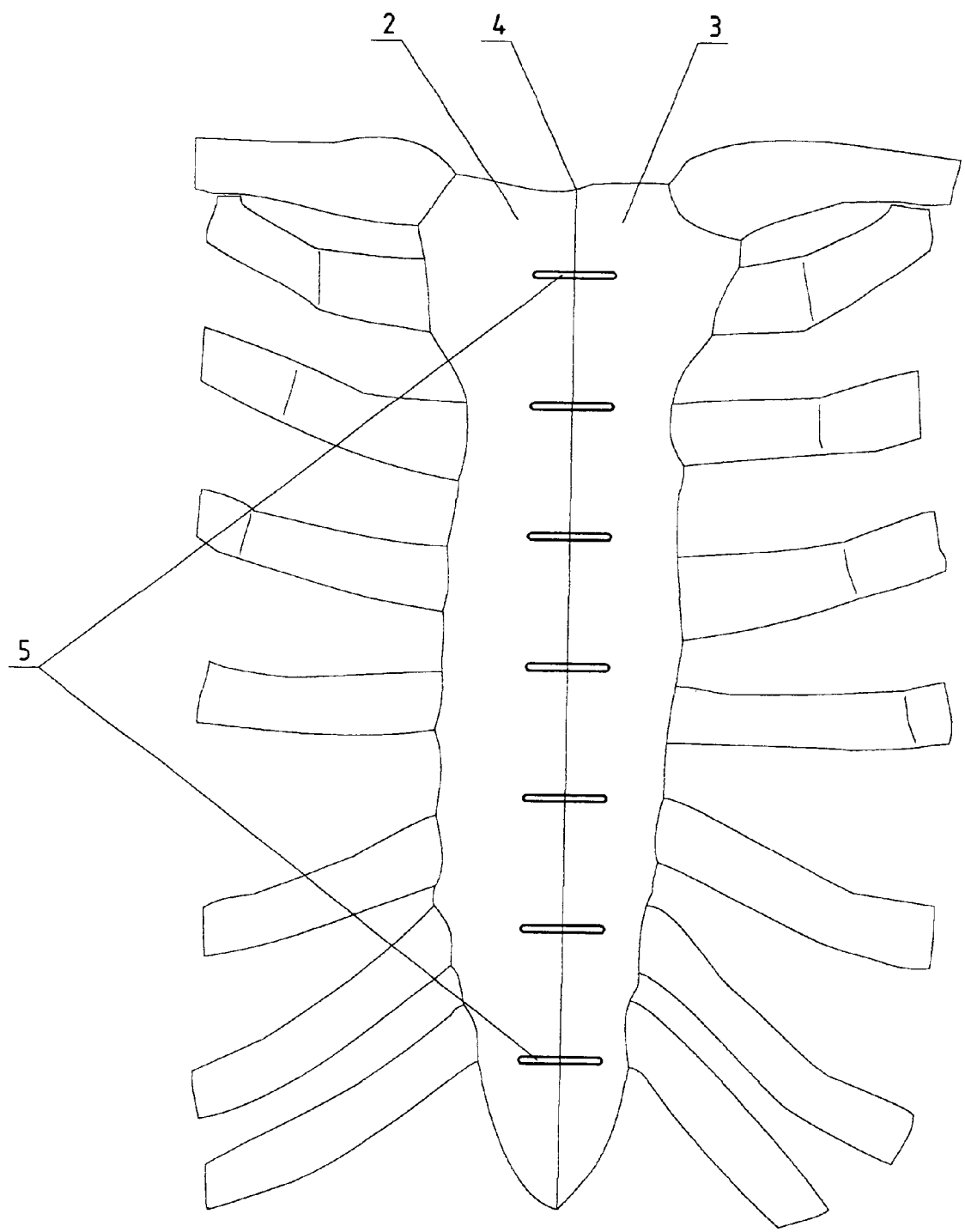
FIG. 15 demonstrates the closed sternum with the set of mounted staples.

When mounting of all required staples 5 is completed (the closed sternum with all mounted staples is shown in FIG. 15), the sternum closure device 1 is removed.

Figure 16:
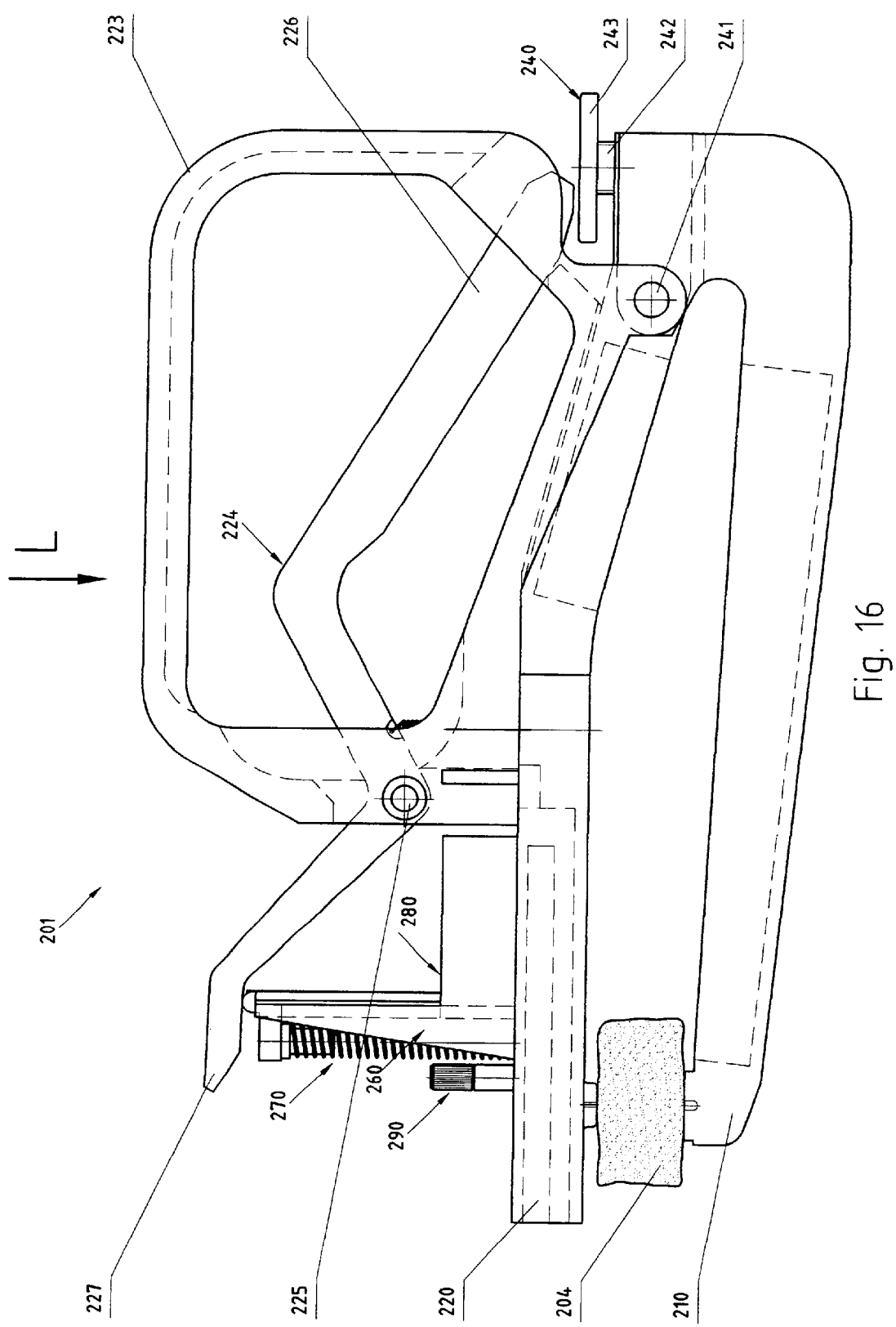
FIG. 16 is a side view of a sternum closure device positioned in the state of drilling openings in the sternum.
Figure 17:
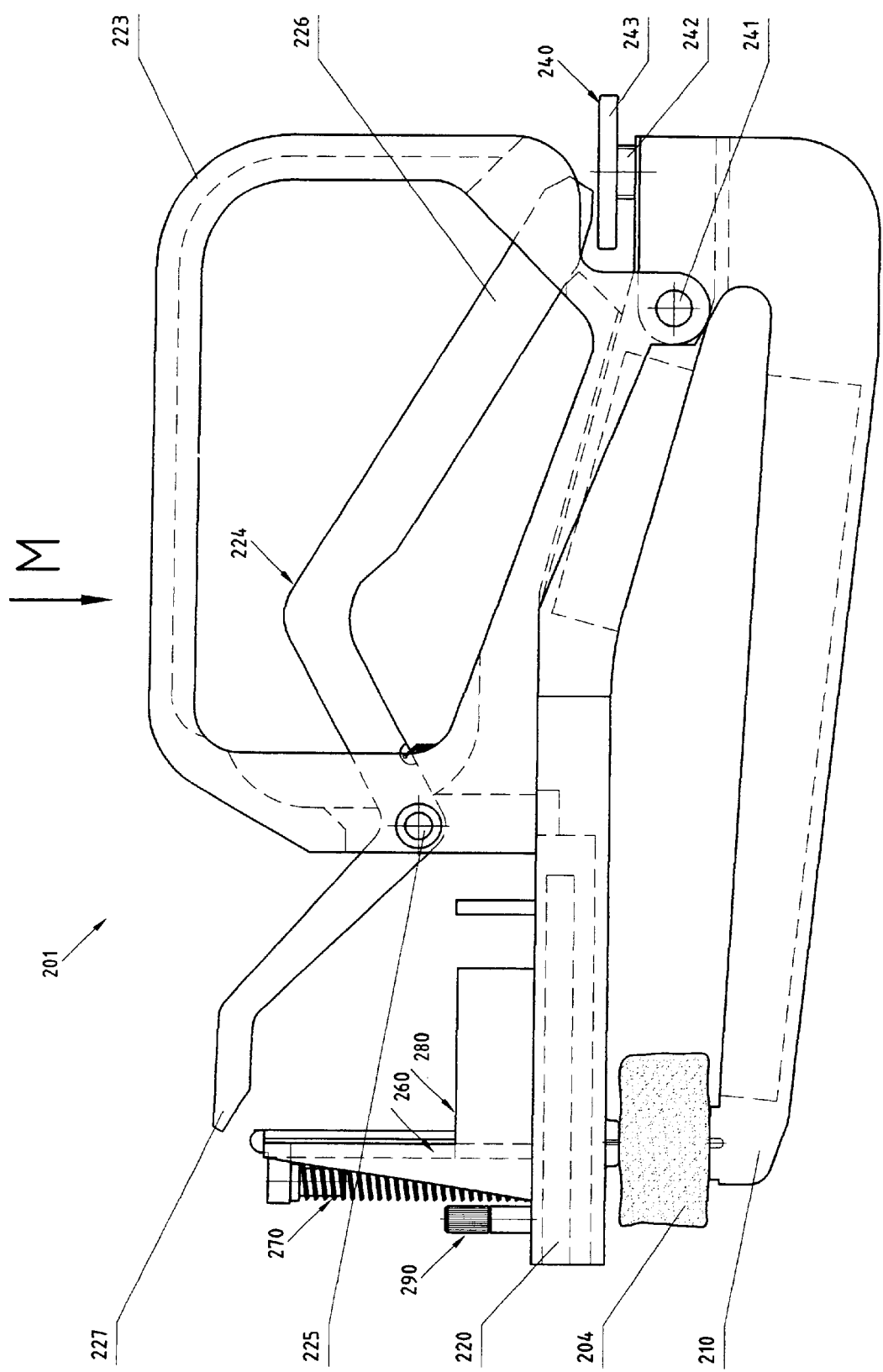
FIG. 17 is a side view of the sternum closure device when it is in the state of mounting staples.
Figure 18:
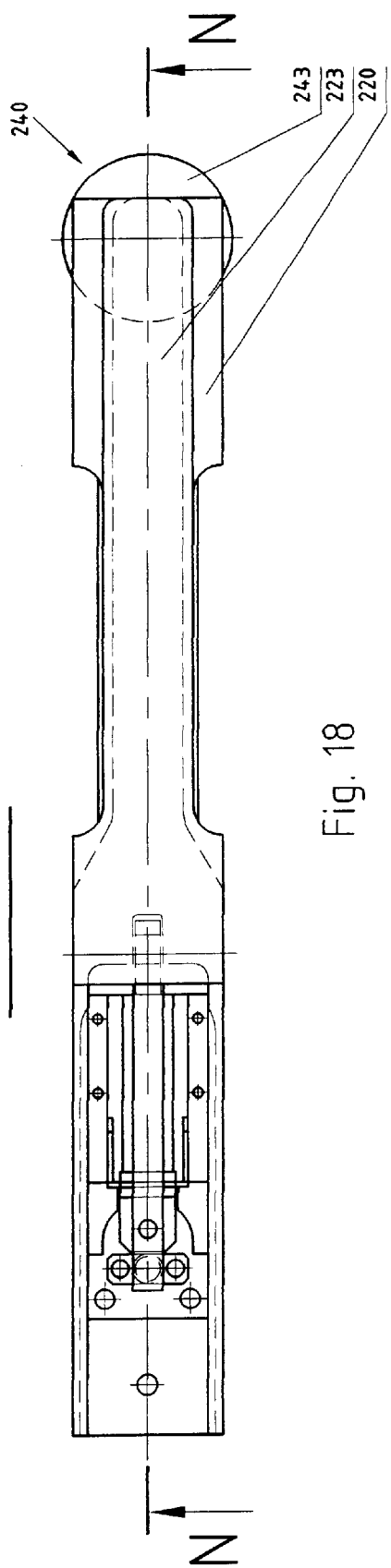
FIG. 18 is a top view of the sternum closure device, taken in the plane of arrow A FIG. 1.
Figure 19:
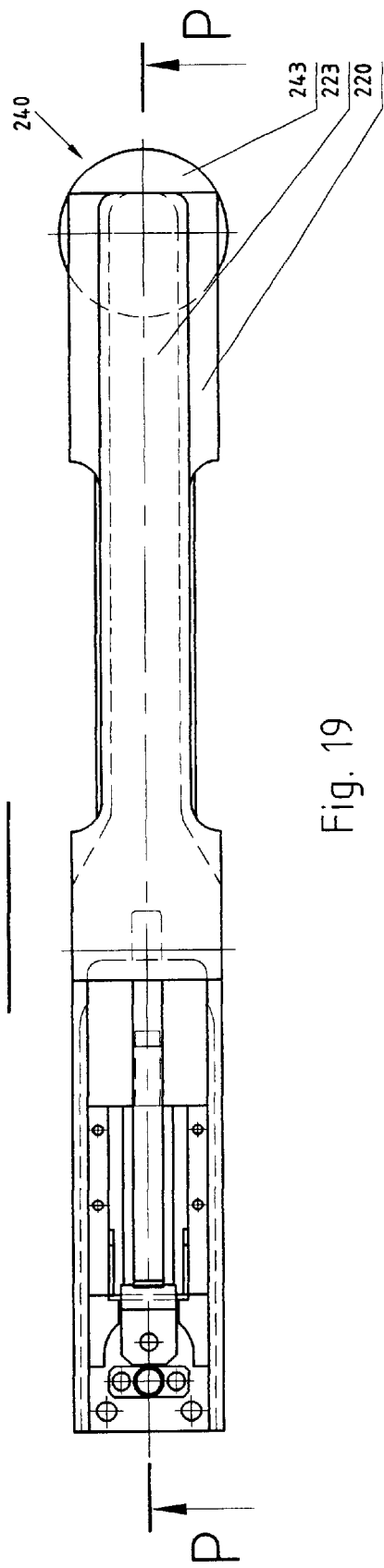
FIG. 19 is a top view of the sternum closure device, taken in the plane of arrow L of FIG. 2.

Referring to FIG. 16, the sternum closure device 1 comprises of an anvil 210 and a bracket 220, the anvil and the bracket are joined together by a displacement mechanism 240. The sternum closure device 1 further comprises of an clamping mechanism 260, which is used for forming openings and mounting the staples 5 in the sternum 4.

Referring to FIGS. 16, 20–24, anvil 210 is provided with two slots 211 and 212 for the purpose of forming staples 5, a opening 213 used for joining the displacement mechanism 240. The bracket 220 comprises of a through slot 221 and a threaded opening 222, said opening 222 serving to join the displacement mechanism 40.

The bracket is joined to the anvil through a displacement mechanism. This mechanism provides turning of the bracket with respect to the anvil. The displacement mechanism comprises of a screw with a handle. This screw is positioned in the threaded opening in the bracket where it is joined to the anvil.

Referring to FIGS. 16–24, the anvil 210 and bracket 220 are joined via the displacement mechanism 240 and are fastened with an axle 241 to enable turning of bracket 220 to and from the anvil 210. The displacement mechanism 240 comprises of screw 242, said screw 242 extending into a handle 243. The screw 242 is fastened through a threaded opening 222 in bracket 220, and is locked rotatable by spherical element 244 in the opening 213 of anvil 210.

Referring to FIGS. 16, 17 20 and 22, the bracket 220 is provided with a handle 223, said handle 223 is installed on the bracket 220. The handle 223 provided a lever 224, the lever 224 is fastened on handle 223 by an axle 225 with possibility of its turning. The lever 224 have two ends 226 and 227, the end 226 is arranged inside the handle 223, the end 227 is free and is arranged from outside the handle 223. In initial position (FIGS. 16,17, 20 and 21) the lever 224 is holding by spring 228. The bracket 20 also is provided with two openings 229 and 230 for fixing the clamping mechanism 260 on the bracket 220.

In a preferred embodiment of the sternum closure device, the clamping mechanism comprises a carrying element, an assembly for mounting staples, a cartridge containing staples, and a lock fixing of the clamping mechanism on the bracket.

The carrying element is constructed as a bed with one rib is situated perpendicularly to the bed surface. The rib is provided with one cut. The bed comprises also two guide-openings.

The assembly for mounting staples is fastened on the bed and is constructed as pressure mechanism comprising the pusher with the transmitting element. The transmitting element being fastened to the pusher.

The cartridge is fastened on the bed and comprises a holder of the staples and means for feeding of the staples.

The lock fixing of the clamping mechanism on the bracket is fastened on the bed and is constructed as a housing comprising a locking element with a handle.

The clamping mechanism 260 consists of the carrying element, which is constructed as the bed 261 with the rib 262 being arranged perpendicularly to the surface of the bed 261, the assembly 270 for mounting staples 5 is fastened on the bed 261, the cartridge 280 containing staples 5 is fastened on the bed 261, and the lock 290 fixing of the clamping mechanism 260 on the bracket 220. The rib 262 of the bed 261 is provided with the cut 263 and the bed 261 comprises two guide-openings 264 and 265.

The assembly 270 for mounting staples 5 constructing as the pressure mechanism comprises the pusher 271 with the transmitting element 272 and spring-wise element 273. The transmitting element 272 being fastened to the pusher 271.

The cartridge 280 is fastened on the bed 261 and comprises a holder 281 of the staples 5 and means 282 for feeding of the staples 5. The means 282 contains a pressure element 283 is placed inside the holder 281. The pressure element 283 comprises a handle 284 and spring-wise element 285.

The lock 290 fixing of the clamping mechanism 260 on the bracket 220 is fastened on the bed 261 and is constructed as a housing 291 comprising a locking element 292 with a handle 293 and spring-wise element 294. The locking element 292 and spring-wise element 294 are placed inside the housing 291.

The bracket 220 comprises also two openings 229 and 230 for fixing the locking element 292 of the lock 290.

The mode of operation of the embodiment of the sternum closure device is described herein below.

Figure 20:
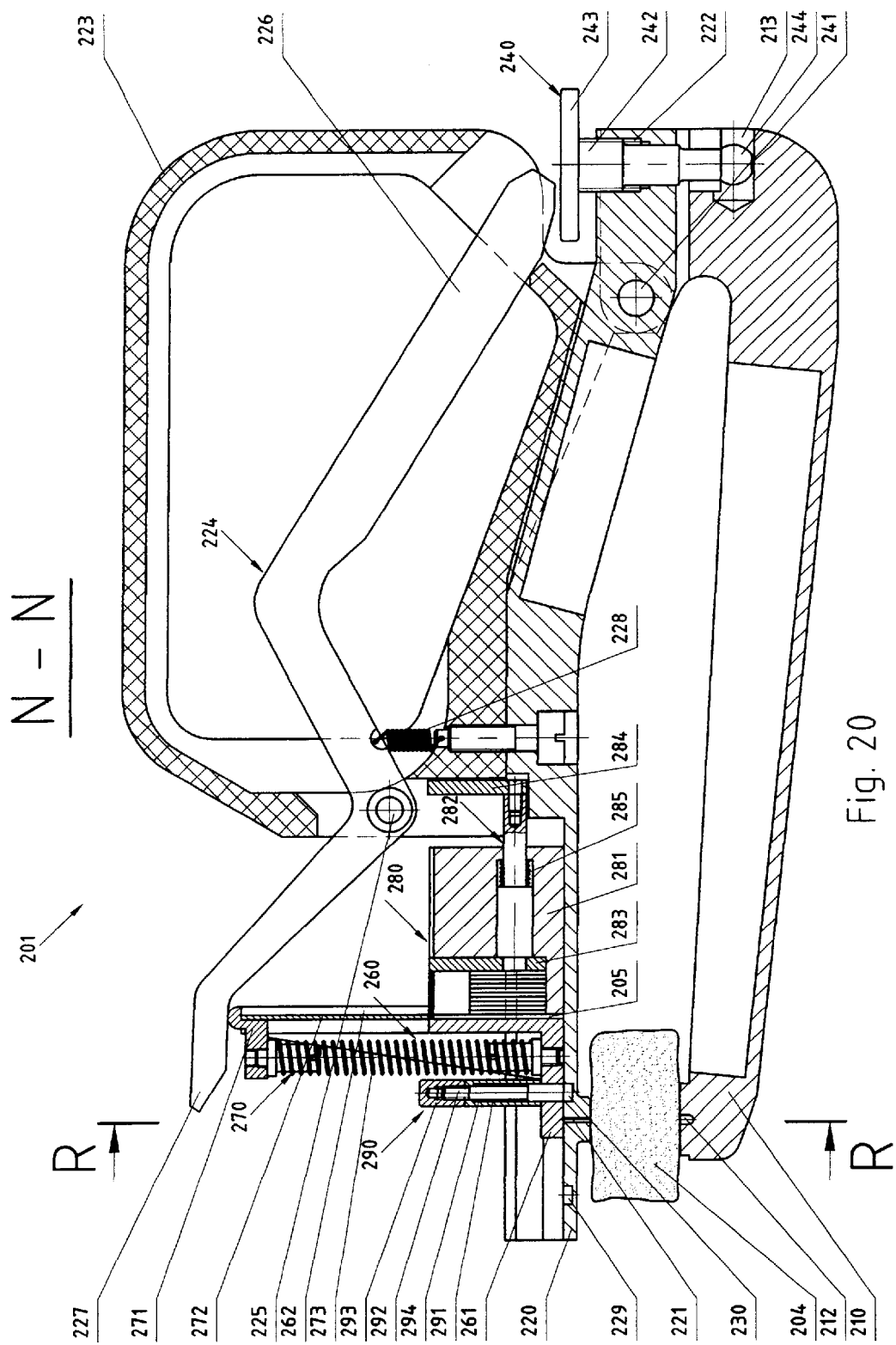
FIG. 20 is a sectional view of the sternum closure device, which is shown in FIG. 18, in the plane of line N—N; this device is in the state preceding drilling the openings in the sternum.
Figure 21:
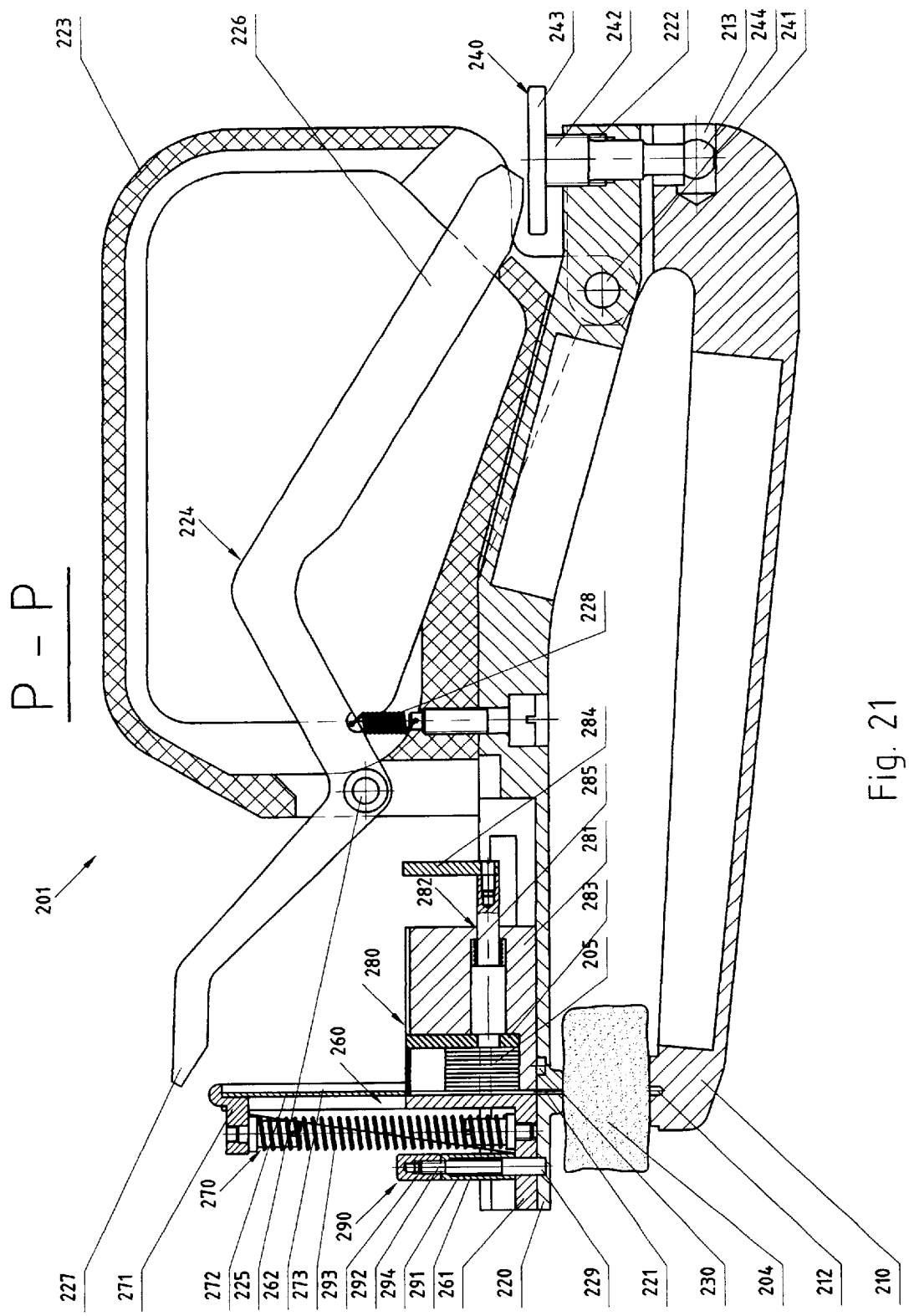
FIG. 21 is a sectional view of the sternum closure device, which is shown in FIG. 19 in the plane of line P—P; this device is in the state preceding mounting the staples in the sternum.

The bracket 220 is turned in direction away from anvil 210 by the displacement mechanism 240 (see FIG. 20). The screw 242 is rotated by handle 243 in threaded opening 222 of the bracket 220, for example, in a counter clockwise direction. Bracket 220 turns around axle 241 in direction away from anvil 210. This results in greater distance between anvil 210 and bracket 220. Anvil 10 and bracket 220 are positioned correspondingly from the internal and external sides of parts 2 and 3 of the severed sternum 4.

With rotation of screw 242 by handle 243 in the opposite direction (in this case—in the clockwise direction), bracket 220 turns around axle 241 towards anvil 210. This motion is accompanied with decrease of the distance between anvil 210 and bracket 220 to contact with the internal and external parts 2 and 3 respectively, of the severed sternum 4.

Figure 5:
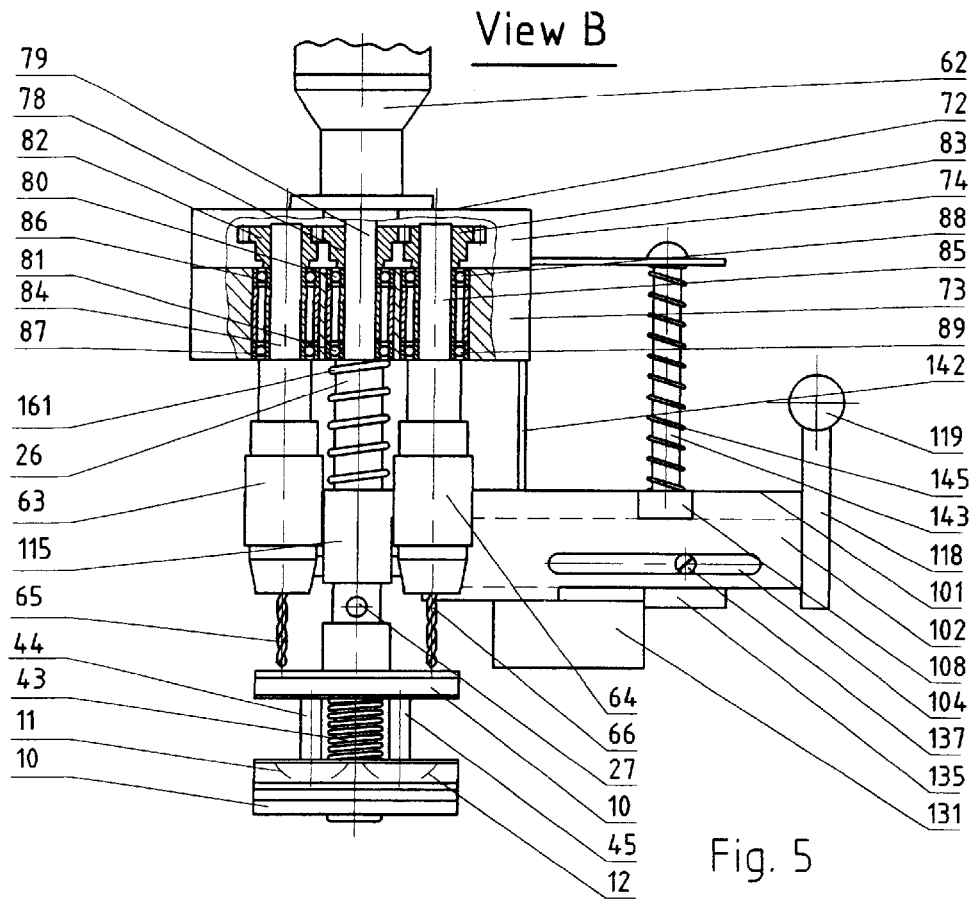
FIG. 5 is a front view of the sternum closure device, taken in the plane of arrow B of FIG. 1.
Figure 6:
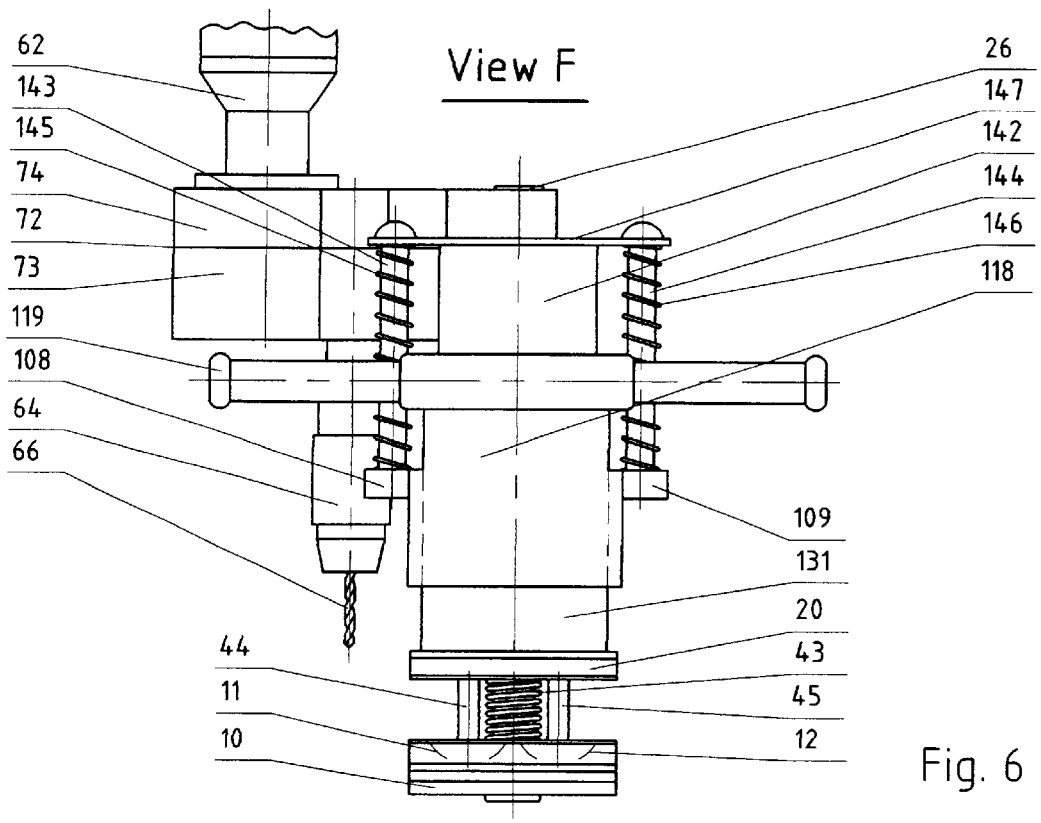
FIG. 6 is a front view of the sternum closure device, taken in the plane of arrow F. of FIG. 3.

The sternum closure device 1 is arranged in the position of drilling openings in parts 2 and 3 of the severed sternum 4 (FIGS. 16, 18, 20 and 23) by lock 290 (FIG. 5). In the initial state spring 294 of lock 290 is released and the locking element 292 is placed in one of two openings 229 or 230 of bracket 220 (in this case—in the opening 230).

Figure 23:
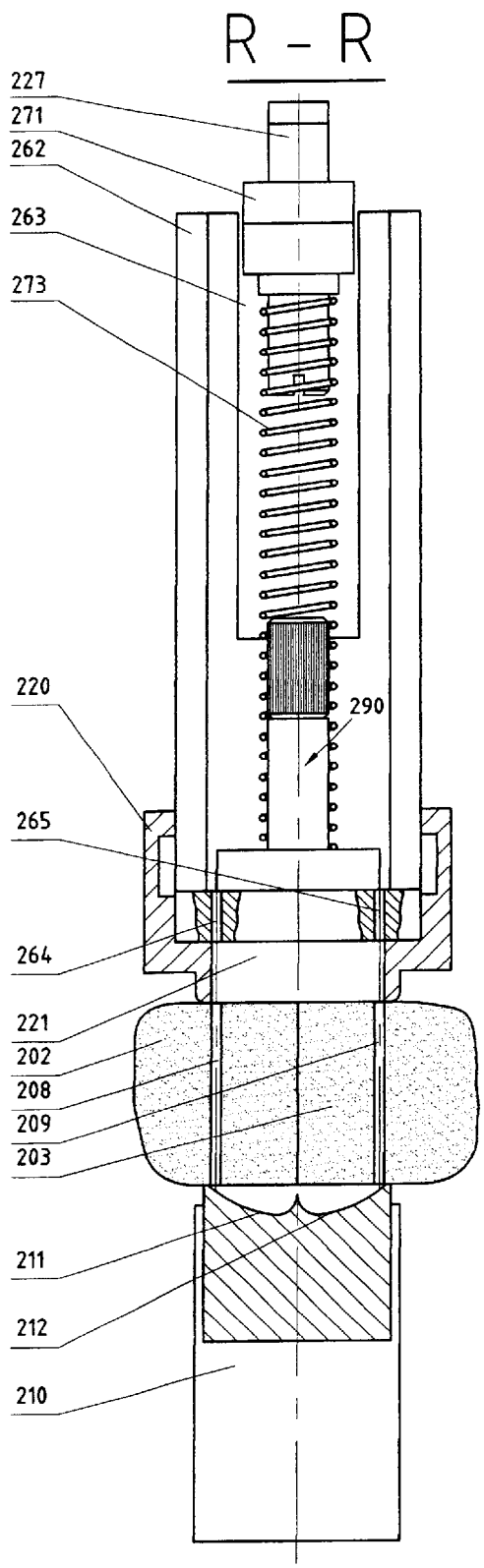
FIG. 23 is a sectional view of the sternum closure device, which is shown in FIG. 20, in the plane of line R—R.

Drilling openings 8 and 9 are performed in parts 2 and 3 of the severed sternum 4 (FIG. 23) by one of any drilling instrument, which are used in sternal surgery (for example, pneumating bit brace—not shown on the drawings). Openings 8 and 9 are drilled by turns correspond to two parts 2 and 3 of the severed sternum 4 through two guide-openings 264 and 265 of bed 261 of clamping mechanism 260 (FIG. 23).

Figure 22:
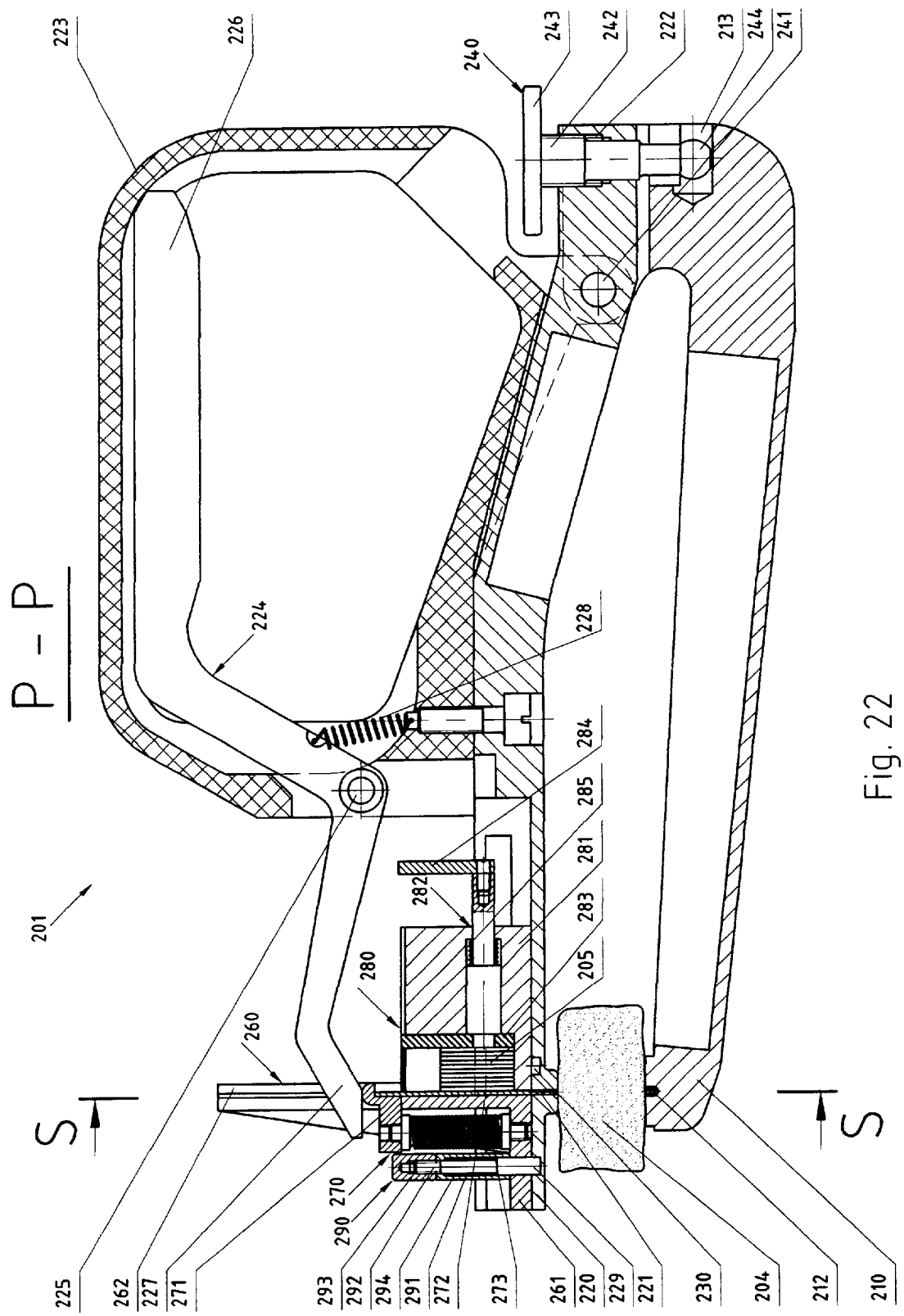
FIG. 22 is a sectional view of the sternum closure device, which is shown in FIG. 19, in the plane of line P—P; this device is in the process of mounting the staples.

After drilling openings 8 and 9 the clamping mechanism 60 is transferred in the state of mounting staples 5 in sternum 4 (FIGS. 17, 19, 21, 22, 24) by lock 290 (FIGS. 20, 22). The locking element 292 is removed from the opening 230 of the bracket 220 by means of lifting the handle 293 compressing spring 294. Then move the clamping mechanism 260 along the bracket 220 until the opening 230 of the bracket 220. With descending handle 293 the compressed spring 294 releases and the locking element 292 sets in the opening 229 of the bracket 220.

Figure 24:
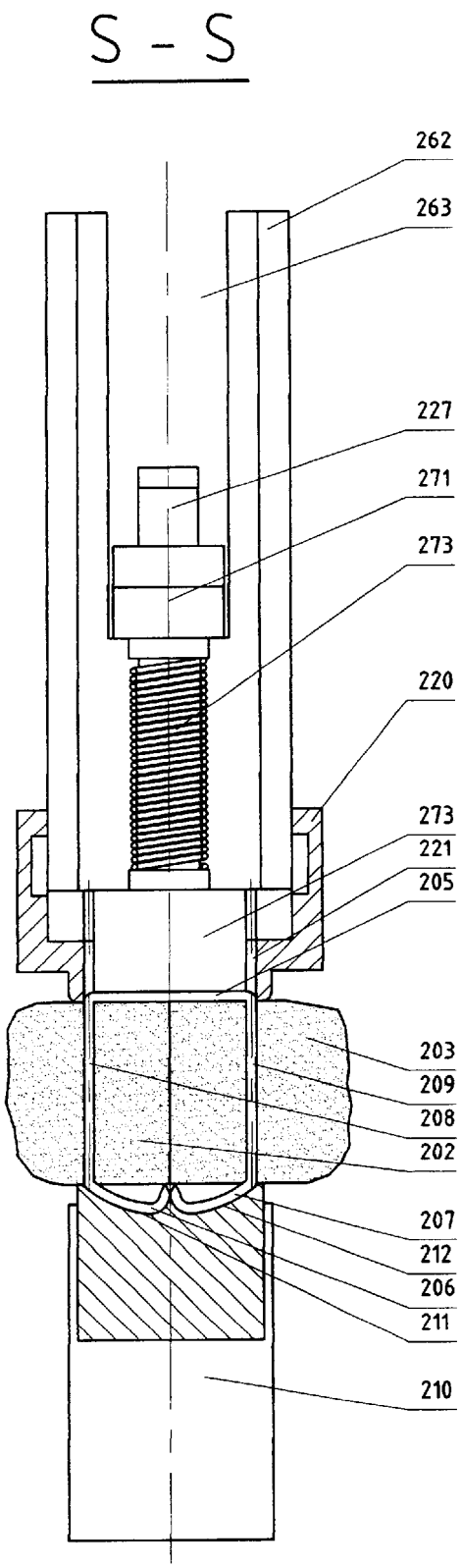
FIG. 24 is a sectional view of the sternum closure device, which is shown in FIG. 22, in the plane of line S—S.

Mounting staples 5 in the through openings 8 and 9 in respective parts 2 and 3 of the severed sternum 4 (FIGS. 22, 24) is performed by assembly 270. Before mounting staples the cartridge 80 is filling in the staples 5. The filling of the staples accomplishes with displacement to back of handle 284 of the means 282 compressing spring 285. The staples 5 are setting on the holder 281. With descending handle 284 the compressed spring 285 pushes out the pressure element 283, which pressing of the staples 5 to rib 262 of the bed 261. With raising of the lever 224 by the end 226 (FIG. 22) the spring 228 is stretching, and the lever 224 turns around the axle 225. The free end 227 of the lever 224 presses to the pusher 271 of the assembly 270 compressing the spring 273. The pressure passes by the transmitting element 272 to the staple 5. The first staple 5 is introduced via the slot 221 of the bracket 220 by its two legs 6 and 7 corresponding to openings 8 and 9 in parts 2 and 3, respectively, of the severed sternum 4. With further pushing on the pusher 271 of the assembly 270, legs 6 and 7 of the staple 5 (FIG. 24) pass via openings 8 and 9. The form of legs 6 and 7 is changed with bending of slots 211 and 212 of the anvil 210, while pulling together parts 2 and 3 of the severed sternum 4 (FIGS. 24, 29).

The angle in which the two legs of the staple bend is circular and effectively secures the two severed parts of the sternum in a stable grip. The present invention is directed to a sternum closure device, which securably retains a plurality of staples around sternum parts to maintain the parts in adjacent engaged relation during healing. The present invention minimizes damage of a tissue stapled and prevents formation of scar tissue.

After mounting of staple 5 is completed raising the end 226 of the lever 224 is terminated. It returns to its initial position owing to release of springs 228. After return the lever 224 to the initial position, the pusher 271, transmitting element 272 and spring 273 of the assembly 270 are released and returned to initial position. With return transmitting element 272 to the initial position, the pressure element 283 of the means 282, which pressing the next staples 5 to rib 262 of the bed 261 and partially releases spring 285.

In order to mount next staples 5, bracket 220 is displaced progressively away from anvil 210 by the displacement mechanism 240. Rotation of screw 242 by handle 243 in the counter clockwise direction allows turning of the bracket 220 relative to the anvil 210 around of the axle 241. It enlarges the distance between anvil 210 and bracket 220.

Then the sternum closure device 1 is made ready for mounting the next staple 5. This process of mounting displacing and compressing staple 5 is repeated as necessary.

Figure 25:
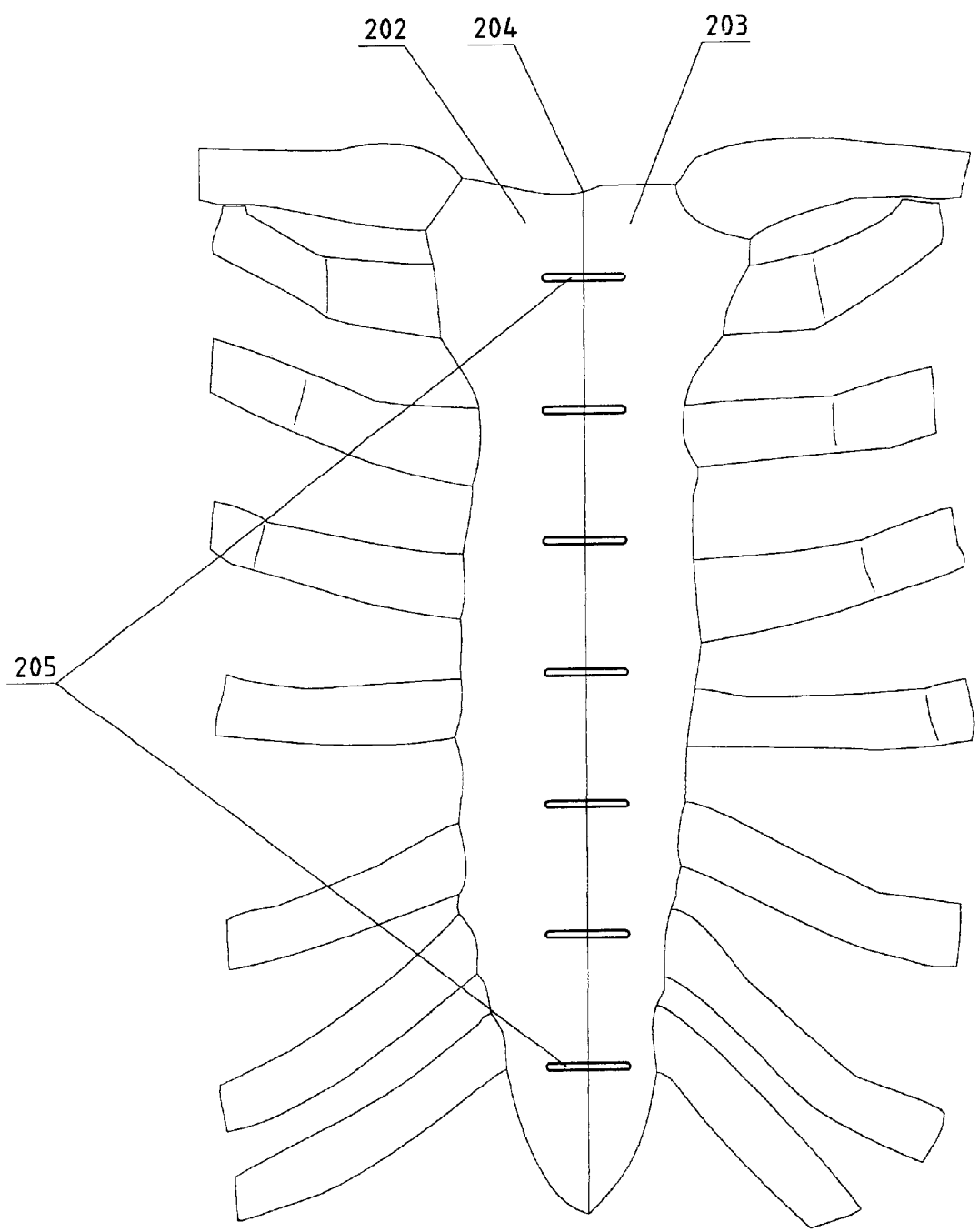
FIG. 25 demonstrates the closed sternum with the set of mounted staples.

When mountings of all required staples 5 is completed (the closed sternum 4 with all mounted staples is shown in FIG. 25) the sternum closure device 1 is removed.

Referring to FIGS. 26 to 33, the pincers 300 are shown to provide a system and method for temporarily joining two parts 2 and 3, of a severed sternum 4, by means of special staples 301, having legs 302 and 303.

Referring to FIGS. 26–28, the pincers 300 comprise of a handle 311 with a jaw 312 is intended for setting of the special staple 301, and a lever 321 with a jaw 322 which is intended for extension of the special staple 301. The handle 311 and the lever 321 are jointed together by an axle 331 which permits turning of the levers, and a spring 332 which facilitates the return in the initial position.

Referring to FIGS. 26–29, the handle 311 is provided with a slot 313 for the purpose of passing the jaw 322 of the lever 321 at the time of its turning. The jaw 312 of the handle 311 is provided a cut section 314 for setting of the special staple 301. The jaw 322 of the lever 321 comprises of a opening 323 for holding of the special staple 301.

Referring to FIGS. 30–31, the special staple 301 is provided with the legs 302 and 303. The leg 302 is changeable, any leg 302 may have a different length, the length of the leg 302 being selecting in accordance with the width of the severed sternum 4. The length of the leg 303 is constant. The legs 302 and 303 are provided with threaded parts 304 and 305 respectively. The legs 302 and 303 are installed in a holder 306, which comprises two openings 307 and 308. The special staple 301 also comprises a spring 309 and a nut 310. The leg 302 by its threaded part 304 is screwed into threaded opening 307, and the leg 303 is inserted into the holder through the opening 308. The spring 309 is installed inside the holder through the opening 308 from one side to the opposite side of the leg 308. The spring 309 is fastened by means the nut 310.

The mode of the operation of the pincers for mounting staples is described herein below.

In initial position the special staple 301 is installed in the pincers 300 so that the threaded part 305 of the leg 303 is put into opening 323 of the jaw 322, and the other side of the leg 303 is put into cut 314 of the jaw 312 (see FIG. 29).

By pushing in the direction of the arrow PUSH onto the lever 321, it turns around the axle 331. The spring 332 compresses, and the jaw 322 presses on the threaded part 305 of the leg 303. The spring 309 compresses and the leg 303 pulls out from the opposite side of the opening 308, while a distance between free ends of the legs 302 and 303 is extending. In this position the pincers 300 with the special staple 301 are set on the severed sternum 4 (see FIG. 32). After setting of the special staple 301 on the severed sternum 4, the lever 321 is released in direction of arrow RELEASE. The spring 332 is released, the lever 321 is turned around the axle 331 backwards, the spring 309 of the special staple 301 is released also, and the legs 302 and 303 are pressed to the parts 2 and 3 the severed sternum 4 (see FIG. 33). The pincers 300 are removed from the special staple 301.

For the mounting of the next special staples 301, the operation is repeated.

Referring to FIGS. 24 to 32, a sternum closure device 1 is shown to provide a system and method for joining two parts 2 and 3, of a severed sternum 4, by means of staples 5, having legs 6 and 7, which are inserted through openings 8 and 9 of the severed sternum 4.

A preferred embodiment of the sternum closure device includes an anvil for forming staples. This anvil is positioned on the internal side of the severed sternum. A bracket is situated on the outer side of the severed sternum, opposite the anvil. The anvil comprises an element for forming the staples. It is designed to have one slot. In addition, the bracket has a second slot which is intended to guide the drills and for mounting the staples on the sternum.

The unique feature about the present invention is that the anvil and the bracket are fastened with the axle and are jointed by means of the displacement mechanism that provides reliable holding of the device on the severed sternum.

The second unique feature about the present invention is that the lever is fastened in the handle of the bracket such that facilitates mounting of the staples on the severed sternum.

Referring to FIGS. 34 to 37, the sternal approximator bracket 401 is shown to provide a system and method for temporary or permanent joining two parts 2 and 3, of a severed sternum 4, by means of sternal approximator brackets 401, having legs 402 and 403.

Referring to FIGS. 34, 35 said leg 403 comprises the threaded stud 404 and nut 405. Said leg 402 consists non-through rectangular opening 406 and through opening 407. Said leg 403 inserted into said opening 406, said stud 404 inserted into said opening 407 and prominent part of said stud 404 and screwed with said nut 405.

The mode of operation of the sternal approximator bracket is described herein below.

In initial position said leg 403 of the sternal approximator bracket 401 is positioned into said leg 402 so that said stud 404 projects from said leg 402 and screwed with said nut 405 (see FIG. 34).

With setting said sternal approximator bracket 401 on said severed sternum 4 said legs 402 and 403 slide apart by unscrew said nut 405 (see FIG. 36). Then said sternal approximator bracket 401 is installing on said severed sternum 4 and said nut 405 is screwing along said stud 404 by any spanner or ratchet, which gives the best fit. Said parts 2 and 3 said severed sternum 4 are pressing tightly and fixing (see FIG. 37).

Removing said sternal approximator bracket 401 from said severed sternum 4 executes in the back order.

The present invention provides a relatively simple and less traumatic means to effect sternum closure which can be performed rapidly and effectively by the surgeon. While the above description contains many specifics, these specifics should not be construed as limitations on the scope of the invention, but merely as exemplification of preferred embodiments thereof. Those skilled in the art will envision many other possible variations that are within the scope and spirit of the invention as defined by the claims appended hereto.

What is claimed is:

1. A specially designed staple, said staple comprising:
    a plurality of legs, each of said legs having a threaded part,
    a holder having two openings, said openings providing entry points for installing the legs, and a spring attached to the holder and being fastened by a nut.

2. A sternum closure device for securing two parts of a severed sternum having an external and internal side, said device comprising:
    an anvil positionable on said internal side of said severed sternum, said anvil being used for forming staples,
    a bracket positionable on said external side of said severed sternum, and a clamping means secured to said device, and wherein said bracket is provided a handle which is installed on said bracket.

3. The sternum closure device as claimed in claim 2, wherein at least one opening comprising in said bracket is constructed as threaded opening.

4. The sternum closure device as claimed in claim 2, wherein said handle provided a lever, said lever is fastened in said handle with possibility of its turning.

5. The sternum closure device as claimed in claim 4, wherein said lever is fastened on said handle with possibility of its turning.

6. A sternum closure device for securing two parts of a severed sternum having an external and internal side, said device comprising:
    an anvil positionable on said internal side of said severed sternum, said anvil being used for forming the staples,
    a bracket positionable on said external side of said severed sternum, and a clamping mechanism, wherein said anvil and said bracket are fastened with an axle and are joined mutually with a displacement mechanism, and wherein said displacement mechanism provides a turning of said bracket relatively of said anvil around of said axle.

7. The sternum closure device as claimed in claim 6, wherein said displacement mechanism comprises a screw with a handle, said screw is arranged in said threaded opening of said bracket, said screw is installed in said opening of said anvil with possibility of its rotation.

8. The sternum closure device as claimed in claim 7, wherein said screw is arranged in said threaded opening of said bracket, said screw is installed in said opening of said anvil with possibility of its rotation.

9. The sternum closure device as claimed in claim 8, wherein said screw is installed in said opening of said anvil with possibility of its rotation.

10. A sternum closure device for securing two parts of a severed sternum having an external and internal side, said device comprising:
    an anvil positionable on said internal side of said severed sternum, said anvil being used for forming the staples,
    a bracket positionable on said external side of said severed steam, and a clamping mechanism, wherein said clamping mechanism is installed on said bracket providing reciprocating displacement, wherein said clamping mechanism comprises:
    a carrying element,
    an assembly for mounting said staples,
    a cartridge containing said staples, and
    a lock fixing said clamping mechanism on said bracket.

11. The sternum closure device as claimed in claim 10, wherein said carrying element is constructed as a bed with at least one rib.

12. The sternum closure device as claimed in claim 11, wherein said rib being arranged perpendicularly to the surface of said bed.

13. The sternum closure device as claimed in claim 12, wherein said rib is provided with at least one cut.

14. The sternum closure device as claimed in claim 11, wherein said bed comprises at least one guide-opening.

15. The sternum closure device as claimed in claim 10, wherein said assembly for mounting said staples is fastened on said carrying element.

16. The sternum closure device as claimed in claim 15, wherein said assembly for mounting said staples is constructed as pressure mechanism.

17. The sternum closure device as claimed in claim 16, wherein said pressure mechanism comprises a pusher with a transmitting element.

18. The sternum closure device as claimed in claim 17, wherein said transmitting element being fastened to said pusher.

19. The sternum closure device as claimed in claim 10, wherein said cartridge is fastened on said carrying element.

20. The sternum closure device as claimed in claim 19, wherein said cartridge comprises a holder of said staples.

21. The sternum closure device as claimed in claim 20, wherein said holder is provided with means for feeding of said staples.

22. The sternum closure device as claimed in claim 10, wherein said lock is fastened on said carrying element.

23. The sternum closure as claimed in claim 22, wherein said lock is constructed as a housing comprising a locking element with a handle.

24. The sternum closure device as claimed in claim 10, wherein said lock is fastened on said carrying element.

25. The sternum closure device claimed in claim 24 wherein the approximating brackets have a low profile and is useful in holding two halves of a severed sternum until union of the halves is achieved.

* * * * *